United States Patent [19]
Imashiro et al.

[11] Patent Number: 6,124,398
[45] Date of Patent: Sep. 26, 2000

[54] CARBODIIMIDE CROSSLINKING AGENT, PROCESS FOR PREPARING THE SAME, AND COATING MATERIAL COMPRISING THE SAME

[75] Inventors: Yasuo Imashiro; Ikuo Takahashi; Naofumi Horie; Takeshi Yamane; Shigekazu Suzuki, all of Tokyo, Japan

[73] Assignee: Nisshinbo Industries, Inc., Tokyo, Japan

[21] Appl. No.: 09/076,714

[22] Filed: May 13, 1998

[30] Foreign Application Priority Data

May 16, 1997 [JP] Japan ..................................... 9-143577

[51] Int. Cl.$^7$ ....................................................... C08F 8/00

[52] U.S. Cl. ............................................................. 525/61

[58] Field of Search ................................. 525/61

[56] References Cited

FOREIGN PATENT DOCUMENTS

| | | |
|---|---|---|
| 2071595 | 10/1995 | Australia . |
| 277361 A1 | 8/1988 | European Pat. Off. . |
| 449143 A2 | 10/1991 | European Pat. Off. . |
| 686626 A1 | 12/1995 | European Pat. Off. . |
| 4410557 A1 | 9/1995 | Germany . |
| 56-143280 | 11/1981 | Japan . |

*Primary Examiner*—Terressa M. Boykin

[57] ABSTRACT

A carbodiimide crosslinking agent comprises, as its main component, a decarbonated condensate of (A) one or more isocyanates selected from isocyanates having at least two isocyanate groups bonded to the carbon of the methylene group in the molecule, and (B) one or more isocyanates selected from alicyclic or aliphatic diisocyanates other than those defined in (A). The condensate is blocked at terminal isocyanates thereof with a hydrophilic group. A process for preparing the crosslinking agent, and a coating material comprising the agent are also described, along with a specific type of crosslinking agent for polyvinyl alcohols.

9 Claims, No Drawings

CARBODIIMIDE CROSSLINKING AGENT, PROCESS FOR PREPARING THE SAME, AND COATING MATERIAL COMPRISING THE SAME

BACKGROUND OF THE INVENTION

This invention relates to a carbodiimide crosslinking agent having good solubility or dispersibility in water, its preparation, and a coating material comprising the crosslinking agent. More particularly, the invention relates to a carbodiimide crosslinking agent which is suitable for crosslinking high molecular weight resins having a group capable of reacting with the carbodiimide group such as a carboxyl group, an amino group, or an alcoholic hydroxyl group, e.g. polyester resins, acrylic resins, polyvinyl alcohol resins and the like, and also to a process for preparing the agent. The invention also relates to a coating material comprising the carbodiimide crosslinking agent which can form coating films having good water, chemical and wear resistances and can be used in various fields of inks, coatings, sealants, adhesives, leather coatings, binders for non-woven fabrics, and the like.

The importance of film-forming methods has been well recognized in the coating industry. Especially, in film-forming techniques, it is the usual practice to add crosslinking agents to film-forming coating compositions so as to impart important characteristic properties such as hardness and solvent, water and wear resistances to the resultant film.

In this case, the conventional crosslinking agents include aziridine compounds, epoxy compounds, blocked isocyanate compounds, and oxazoline compounds. These crosslinking agents which have bi- or polyfunctional groups are mixed with organic compounds (typically high molecular weight resins) having a functional group capable of reacting with the functional group such as a carboxyl group, an amino group or an alcoholic hydroxyl group, prior to the formation of film. The resultant mixture is coated onto a substrate and cured at a given temperature to form a film. In this way, the crosslinking agent can impart good characteristic properties such as a hardness and solvent, water and wear resistances to the film.

However, the oxazoline compound and the blocked isocyanate compound have a curing temperature as high as 80 to 180° C., thus causing a problem that they are not used for a substrate having a poor heat resistance and that an expensive equipment is necessary. In particular, the blocked isocyanate compound may adversely influence environments and workers because a blocking agent used to block the isocyanate group is so volatile that it is vaporized upon curing.

The aziridine compound and the epoxy compound are disadvantageous in that the storage stability of these compounds is so poor that when preserved under high temperature and high humidity conditions, the compound polymerizes and is converted to a hardened matter, and has very strong toxicity. Thus, care has to be paid in handling of these compounds.

In recent years, various types of carbodiimide compounds have been developed, and attention has been drawn to their good characteristics on use as a crosslinking agent. At present, commercially available carbodiimide compounds exhibit poor miscibility with resins to be crosslinked. Especially, the compounds are not satisfactory with respect to reactivity at low temperatures, thus presenting the problem that desirable physical properties are not imparted to a crosslinked resin.

SUMMARY OF THE INVENTION

An object of the present invention is to provide a carbodiimide crosslinking agent which has good miscibility and reactivity with resins to be crosslinked and is able to form a film which has good resistances to water, chemicals and wear.

Another object of the present invention is to provide a process for preparing such a crosslinking agent and also to provide a coating material formulated with the crosslinking agent.

In order to achieve the above objects, we have made intensive studies on crosslinking agents. As a result, it has been found that a carbodiimide crosslinking agent comprising as a main component thereof a carbodiimide compound, which is prepared by decarbonation reaction of (A) an isocyanate having at least two isocyanate groups bonded to the carbon of the methylene group in the molecule, (B) an alicyclic or aliphatic diisocyanate other than defined in (A), and (C) a monofunctional water-soluble or water-dispersible organic compound in the presence of a catalyst for carbodiimidization and in which terminal isocyanate groups of the resultant decarbonated condensation reaction product of the (A) and (B) components are blocked with a hydrophilic group, has good water solubility and dispersibility as well as high reactivity and good miscibility with resins to be crosslinked. Moreover, the problems, which are involved in the carbodiimide compound derived from the isocyanate compound (A) alone that reactivity becomes extremely high so that a pot life necessary for film formation cannot be satisfactorily obtained and also involved in the carbodiimide compound derived singly from the diisocyanate compound (B) that reactivity and miscibility with polymer resins to be crosslinked are low with a poor crosslinking effect, can be effectively solved.

More particularly, it has been found that a crosslinking agent comprising as its main component a carbodiimide compound derived from (A) one or more isocyanates each having at least two isocyanate groups bonded to the carbon of the methylene group in the molecule, preferably bifunctional isocyanates such as hexamethylene diisocyanate (HDI), hydrogenated xylylene diisocyanate ($H_6$XDI), xylylene diisocyanate (XDI), 2,2,4-trimethylhexamethylene diisocyanate (TMHDI), 1,12-diisocyanatododecane (DDI), norbornane diisocyanate (NBDI) and 2,4-bis-(8-isocyanatooctyl)-1,3-dioctyl cyclobutane (OCDI) and (B) one or more alicyclic or aliphatic diisocyanates other than defined in (A) such as 4,4'-dicyclohexylmethane diisocyanate (HMDI), tetramethylxylylene diisocyanate (TMXDI) and isophorone diisocyanate (IPDI), and blocked with (C) a monofunctional water-soluble or dispersible organic compound at terminal isocyanate groups thereof is suitable because of its good water solubility or dispersibility as well as good miscibility with resins to be crosslinked having a group capable of reacting with the carbodiimide group such as a carboxyl group, an amino group or an alcoholic hydroxyl group. The reaction well proceeds at low temperatures, and the agent can impart favorable physical properties to the resultant crosslinked resin. In addition, such an agent has a satisfactorily long pot life.

It has also been found that for crosslinkage of polyvinyl alcohol (PVA) resin, such a crosslinking agent is very suitable, which comprises, as its main component, a water-soluble or dispersible carbodiimide compound having at least one —NCN— group which consists of a condensation reaction product obtained by decarbonation condensation of one or more diisocyanates or a mixture of one or more diisocyanates and one or more triisocyanates and blocked with a hydrophilic group at terminal isocyanate groups, especially, a carbodiimide compound obtained by decarbonation reaction of one or more isocyanates selected from the group consisting of 4,4'-dicyclohexylmethane diisocyanate (HMDI), tetramethylxylylene diisocyanate (TMXDI), isophorone diisocyanate (IPDI), 2,4,6-triisopropylphenyl diisocyanate (TIDI), 4,4'-diphenylmethane diisocyanate (MDI), tolylene diisocyanate (TDI), hydrogenated tolylene diisocyanate (HTDI) and isocyanates having at least two isocyanates bonded to the carbon of a methylene group with a monofunctional water-soluble or dispersible organic compound in the presence of a catalyst for carbodiimidization. The crosslinking agent has good water solubility or dispersibility, good reactivity with PVA resin, and good miscibility with PVA resin, and is able to effectively crosslink PVA resin therewith at low temperatures.

It has been further found that a coating material comprising a resin having a group reactive with the carbodiimide group such as a carboxyl group, an amino group or an alcoholic hydroxyl group and the carbodiimide crosslinking agent can form a film having good hardness and good resistances to water, chemicals and wear. The coating material is particularly suitable for applications as paints, inks, coatings, sealants, adhesives, leather coatings, binders for non-woven fabric, and the like. The invention is accomplished based on these findings.

According to one embodiment of the present invention, there is provided a carbodiimide crosslinking agent comprising, as its main component, a carbodiimide compound which consists essentially of a condensate through decarbonation reaction between (A) one or more isocyanates having at least two isocyanate groups bonded to the carbon of the methylene group in the molecule, and (B) one or more alicyclic or aliphatic diisocyanates other than those isocyanates defined in (A), wherein the condensate is blocked with a hydrophilic group at terminal isocyanate groups thereof.

According to another embodiment of the present invention, there is also provided a crosslinking agent for polyvinyl alcohol comprising, as its main component, a water-soluble or dispersible carbodiimide compound which consists essentially of a condensate obtained through decarbonation condensation of one or more diisocyanates or a mixture of at least one diisocyanate and at least one triisocyanate, wherein the condensate is blocked with a hydrophilic group at terminal isocyanate groups thereof.

According to a further embodiment of the present invention, there is provided a process for preparing a carbodiimide crosslinking agent comprising subjecting (A) one or more isocyanates having at least two isocyanate groups bonded to the carbon of the methylene group in the molecule, (B) one or more alicyclic or aliphatic diisocyanates other than those defined in (A), and (C) a monofunctional water-soluble or dispersible organic compound to decarbonation condensation reaction in the presence of a carbodiimidizing catalyst.

According to a still further embodiment of the present invention, there is provided a coating material or composition comprising a resin having a group capable of reacting with a carbodiimide group, and the carbodiimide crosslinking agent defined in the above embodiments.

DETAILED DESCRIPTION OF THE INVENTION

The carbodiimide crosslinking agent of the present invention is mainly composed of a carbodiimide compound consisting essentially of a decarbonation condensation reaction product of (A) one or more isocyanates each having at least two isocyanate groups bonded to the carbon of the methylene group in the molecule, and (B) one or more alicyclic and/or aliphatic diisocyanates other than those defined in (A), the condensation reaction product being blocked with a hydrophilic group at terminal isocyanate groups, especially, by use of (C) a monofunctional water-soluble or dispersible organic compound.

The isocyanates of component (A) should be ones having at least two isocyanate groups bonded to the carbon of the methylene group in the molecule, and are preferably bifunctional diisocyanates. Compounds having three or more isocyanate groups may be used in combination with diisocyanates. The isocyanates may be either aliphatic, alicyclic or aromatic. The isocyanates include, for example, hexamethylene diisocyanate (HDI), hydrogenated xylylene diisocyanate ($H_6XDI$), xylylene diisocyanate (XDI), 2,2,4-trimethylhexamethylene diisocyanate (TMHDI), 1,12-diisocyanatododecane(DDI), norbornane diisocyanate (NBDI) and 2,4-bis-(8-isocyanatooctyl)-1,3-dioctyl cyclobutane (OCDI), which may be used singly or in combination of two or more.

The isocyanates of component (B) should be alicyclic isocyanates or aliphatic isocyanates other than those isocyanates defined in (A), and should preferably be diisocyanates having two isocyanate groups in the molecule. Such isocyanates include 4,4'-dicyclohexylmethane diisocyanate (HMDI), tetramethylxylylene diisocyanate (TMXDI) and isophorone diisocyanate (IPDI), which may be used singly or in combination.

The mixing ratio (by mole) between the isocyanate groups of the isocyanate (A) and the isocyanate groups of the isocyanate (B) is in the range of 50:1 to 1:20, preferably 20:1 to 1:10. If the mixing ratio is larger than 50:1, the pot life is so short that handling is difficult. When the ratio is smaller than 1:20, the crosslinking effect of the resultant carbodiimide lowers.

The monofunctional water-soluble or dispersible organic compound of component (C) is used to impart solubility or dispersibility in water to the carbodiimide compound. The compound should be one which has monofunctionality and can react with the terminal isocyanate groups of the carbodiimide compound derived from the isocyanate (A) and the isocyanate (B) to block the terminal groups. Such water-soluble or water-dispersible organic compounds may be any compounds which have one group capable of reacting with an isocyanate group, e.g. OH group, COOH group, $NH_2$ group or $SO_3H$ group, and which are soluble or dispersible in water. The compounds include, for example, monoalkyl esters and monoalkyl ethers of bifunctional, water-soluble or water-dispersible organic compounds having preferably OH groups at terminal ends thereof, e.g. polyethylene glycol, polypropylene glycol and the like, and monofunctional organic compounds having a cationic functional group (e.g. a group containing nitrogen) or an anionic functional group (e.g. a group containing a sulfonyl group). Specific examples preferably include polyethylene glycol monomethyl ether, polypropylene glycol monomethyl ether, and the like.

The water-soluble or dispersible organic compound (C) is added such that a mixing ratio between the total isocyanate groups in the total isocyanates of (A) and (B) and the functional groups of the water-soluble or dispersible organic compound capable of reacting with the isocyanate groups is from 1.1:1 to 16:1 (with a theoretical degree, n, of polymerization of carbodiimide being n=0.1 to 15), preferably from 1.5:1 to 11:1 (with the degree, n, of polymerization being n=0.5 to 10), and more preferably, from 2:1 to 6:1 (with the degree, n, of polymerization being n=1 to 5). If the mixing ratio is smaller than 1.1:1, water solubility increases, resulting in poor water resistance. On the contrary, when the ratio exceeds 16:1, water is unlikely to disperse, so that the effect as a crosslinking agent may lower.

The carbodiimide compound can be prepared by condensation reaction (carbodiimidization reaction) of a mixture of the components (A), (B) and (C) through decarbonation.

The carbodiimidization reaction may be carried out by a known procedure. More particularly, an isocyanate (A), an isocyanate (B), and a monofunctional water-soluble or dispersible organic compound (C) are mixed at given ratios within the above-defined range. A catalyst for carbodiimidization is added to the mixture, which may be dissolved in an inert solvent or may be in a solvent-free condition, in a stream of an inert gas such as nitrogen or under bubbling conditions, followed by heating at a reaction temperature of 150 to 200° C. under agitation, thereby causing condensation reaction (carbodiimidization reaction) through decarbonation to proceed. In this case, the completion of the reaction is judged by measurement of infrared (IR) absorption spectra, confirming that an absorption of the isocyanate group at a wavelength of 2200 to 2300 $cm^{-1}$ disappears.

Alternatively, the carbodiimidization reaction may be carried out by mixing the monofunctional water-soluble or dispersible organic compound (C) with the isocyanate (A) prior to the addition of the isocyanate (B), and, if necessary, agitating in a stream of an inert gas within a temperature range of 0 to 200° C. or under bubbling conditions for a given time, followed by further adding the isocyanate (B) and mixing under agitation.

The catalysts for carbodiimidization should preferably be organophosphorus compounds. From the standpoint of activity, phosphorene oxides are preferred. Specific examples include 3-methyl-1-phenyl-2-phosphorene-1-oxide, 3-methyl-1-ethyl-2-phosphorene-1-oxide, 1,3-dimethyl-2-phosphorene-1-oxide, 1-phenyl-2-phosphorene-1-oxide, 1-ethyl-2-phosphorene-1-oxide, 1-methyl-2-phosphorene-1-oxide, and double-bond isomers thereof. Of these, industrially, readily available 3-methyl-1-phenyl-2-phosphorene-1-oxide is preferred. In this case, the amount of the catalyst usually ranges 0.1 to 10% by weight, preferably from 0.5 to 5% by weight, based on the total amount of the components (A), (B) and (C).

The carbodiimide compound obtained in this way is a main component of a carbodiimide crosslinking agent of the present invention. The crosslinking agent is added to and mixed with polymer resins having a functional group capable of reacting with the carbodiimide group such as a carboxyl group, an amino group, an alcoholic hydroxyl group, a thiol group, or the like. The resins include water-soluble acrylic resins, polyester resins, polyurethane resins, and polyvinyl alcohol (PVA) resins. There can be obtained coating materials of the present invention. The crosslinking agent of the present invention has good water solubility or dispersibility, and good miscibility with polymer resins, reacts sufficiently with the resins at low temperatures, and can impart desirable physical properties to the resultant crosslinked resins. In addition, an expensive equipment is unnecessary. The amount of the carbodiimide crosslinking agent is appropriately controlled depending on the type of polymer resin and is not critical, and is generally in the range of about 0.1 to 50 parts by weight per 100 parts by weight of a polymer resin.

The crosslinking agent for PVA may comprise, as its main component, a water-soluble or dispersible carbodiimide compound consisting essentially of a decarbonated condensation reaction product of a diisocyanate or a mixture of a diisocyanate and a triisocyanate, which has at least one —NCN— group and wherein the terminal isocyanates are blocked with a hydrophilic group.

The isocyanate used herein may be an isocyanate (A) or an isocyanate (B) alone, or a mixture of an isocyanate (A) and an isocyanate (B). The other starting materials and a preparation process are similar to those described before.

It will be noted that PVA resins may be those which are partially saponified, completely saponified, cation-modified, and anion-modified. Of these, modified polyvinyl alcohol is preferred, which is obtained by saponifying a copolymer between an ethylenically unsaturated monomer having a carboxyl group, a sulfonate group or an ammonium base and a vinyl ester.

Examples of the ethylenically unsaturated monomer having a carboxyl group include ethylenically unsaturated carboxylic acids, salts thereof, lower alkyl esters thereof and acid anhydrides thereof, such as crotonic acid, itaconic acid, monomethyl maleate, acrylic acid, methyl acrylate, maleic anhydride and the like. Examples of the ethylenically unsaturated monomers having a sulfonate group include ethylenically unsaturated sulfonic acids and salts thereof, such as vinylsulfonic acid, allylsulfonic acid, N-(meth)acrylamidopropanesulfonic acid, and the like. Examples of the ethylenically unsaturated monomer having an ammonium base include trimethyl-3-(1-(meth)acrylamido-1,1-dimethylpropyl)ammonium chloride, trimethyl-3-(1-(meth)acrylamido-1,1-dimethylethyl)ammonium chloride, trimethyl-3-(1-(meth)acrylamidopropyl)ammonium chloride, N-vinylimidazole, N-vinyl-N-methylimidazole, and quaternarized products thereof. Preferably, the content of the anionic or cationic group moiety in the modified polyvinyl alcohol is in the range of 1 to 10 mole %. Depending on the purpose, other types of ethylenically unsaturated monomers may be copolymerized. In this case, the content of the moiety or moieties of other types of ethylenically unsaturated monomers may be within a range which permits the resultant modified PVA to be soluble in water, and is preferably in the range of 0.1 to 10 mole % although depending on the content of ionic group moieties and the degree of saponification.

The degree of saponification of the vinyl acetate units in the modified PVA may depend on the content of the ionic groups and is within a range permitting the resultant PVA to be soluble in water. Usually, the degree is selected from the range of 50 to 100 mole %, preferably 70 to 99 mole %. The degree of polymerization is not critical, and is preferably in the range of 100 to 3,000.

The amount of the crosslinking agent relative to PVA resin depends on the carbodiimide equivalence (the molecular weight/the number of the carbodiimide groups) in the water-soluble or dispersible carbodiimide compound and the type of the carbodiimide compound. Usually, the amount is in the range of 0.5 to 50 parts by weight, preferably from 1 to 30 parts by weight, of a water-soluble or dispersible carbodiimide compound as a solid matter, based on 100 parts by weight of PVA resin. If the amount is less than 0.5 part by weight, satisfactory crosslinkage may not be attained, and thus, an intended water resistance may not be obtained. On the other hand, if the amount exceeds 50 parts by weight, the crosslinking effect is not further improved, which may result in poor economy.

The coating material of the invention should comprise the polymer resin and the above-described crosslinking agent. In addition to these components, the other optional components such as pigments, fillers, plasticizers, dispersants, coating surface-controlling agents, surfactants, UV absorbers, antioxidants and the like may be added to the coating material. The amount of these optional components should be within a range not impeding the effect of the invention.

The film formed by coating and curing the coating material has good resistances to water, chemicals and wear.

The carbodiimide crosslinking agent of the invention is applicable to inks, sealants, adhesives, binders for non-woven fabric, and other various fields, in addition to the coating material.

EXAMPLE

The invention is more particularly described by way of Synthetic Examples and Examples, which should not be construed as limiting the invention thereto. Comparative examples are also described.

Synthetic Example 1

As shown in Table 1, 1682 g of hexamethylene diisocyanate (HDI) and 2200 g of polyethylene glycol monomethyl ether (M400, with an average molecular weight of 400) were placed in a 20-liter reaction vessel equipped with a reflux condenser and an agitator, and mechanically agitated at 120° C. for 1 hour. Further, 262 g of 4,4'-dicyclohexylmethane diisocyanate (HMDI) and 38.8 g (2 wt % based on the total amount of the isocyanates) of 3-methyl-1-phenyl-2-phosphorene-1-oxide used as a catalyst for carbodiimidization were added to the mixture, followed by further agitation in a stream of nitrogen at 185° C. The completion of reaction was judged by measurement of infrared (IR) absorption spectra, through which an absorption of the isocyanate group at a wavelength of 2200 to 2300 cm$^{-1}$ was confirmed to disappear.

After the completion of the reaction, the reaction system was allowed to cool to 60° C., to which distilled water was added so that the resin solid component was at a level of 5671 g (40 wt %), thereby preparing a carbodiimide compound.

It will be noted that in Tables 1 to 18, the degree of polymerization indicates a theoretical degree of polymerization of each resulting carbodiimide compound.

Synthetic Examples 2 to 5

Carbodiimide compounds of Synthetic Examples 2 to 5 were prepared under the same conditions as in Synthetic Example 1 except that the amounts of HDI and M400 being mixed were changed as shown in Table 1.

TABLE 1

| | HDI (g) | HMDI (g) | M400 (g) | Degree of Polymerization (n) | HDI:HMDI (Molar Ratio) |
|---|---|---|---|---|---|
| Synthetic Example | | | | | |
| 1 | 1682 | 262 | 2200 | 3 | 10:1 |
| 2 | 841 | 262 | 800 | 4 | 5:1 |
| 3 | 505 | 262 | 800 | 3 | 3:1 |
| 4 | 168 | 262 | 800 | 1 | 1:1 |
| 5 | 168 | 262 | 400 | 3 | 1:1 |

Synthetic Examples 6 to 10

Carbodiimide compounds of Synthetic Examples 6 to 10 were prepared under the same conditions as in Synthetic Example 1 according to the formulations shown in Table 2 wherein hydrogenated xylylene diisocyanate ($H_6XDI$) was used in place of HDI in Synthetic Example 1.

TABLE 2

| | $H_6XDI$ (g) | HMDI (g) | M400 (g) | Degree of Polymerization (n) | $H_6XDI$:HMDI (Molar Ratio) |
|---|---|---|---|---|---|
| Synthetic Example | | | | | |
| 6 | 1942 | 262 | 2200 | 3 | 10:1 |
| 7 | 971 | 262 | 800 | 4 | 5:1 |
| 8 | 583 | 262 | 800 | 3 | 3:1 |
| 9 | 194 | 262 | 800 | 1 | 1:1 |
| 10 | 194 | 262 | 400 | 3 | 1:1 |

Synthetic Examples 11 to 15

Carbodiimide compounds of Synthetic Examples 11 to 15 were prepared under the same conditions as in Synthetic Example 1 according to the formulations shown in Table 3 wherein xylylene diisocyanate (XDI) was used in place of HDI in Synthetic Example 1.

TABLE 3

| | XDI (g) | HMDI (g) | M400 (g) | Degree of Polymerization (n) | XDI:HMDI (Molar Ratio) |
|---|---|---|---|---|---|
| Synthetic Example | | | | | |
| 11 | 1882 | 262 | 2200 | 3 | 10:1 |
| 12 | 941 | 262 | 800 | 4 | 5:1 |
| 13 | 565 | 262 | 800 | 3 | 3:1 |
| 14 | 188 | 262 | 800 | 1 | 1:1 |
| 15 | 188 | 262 | 400 | 3 | 1:1 |

Synthetic Examples 16 to 20

Carbodiimide compounds of Synthetic Examples 16 to 20 were prepared under the same conditions as in Synthetic Example 1 according to the formulations shown in Table 4 wherein 2,2,4-trimethylhexamethylene diisocyanate (TMHDI) was used in place of HDI in Synthetic Example 1.

TABLE 4

| | TMHDI (g) | HMDI (g) | M400 (g) | Degree of Polymerization (n) | TMHDI:HMDI (Molar Ratio) |
|---|---|---|---|---|---|
| Synthetic Example | | | | | |
| 16 | 2100 | 262 | 2200 | 3 | 10:1 |
| 17 | 1050 | 262 | 800 | 4 | 5:1 |
| 18 | 630 | 262 | 800 | 3 | 3:1 |
| 19 | 210 | 262 | 800 | 1 | 1:1 |
| 20 | 210 | 262 | 400 | 3 | 1:1 |

Synthetic Examples 21 to 25

Carbodiimide compounds of Synthetic Examples 21 to 25 were prepared under the same conditions as in Synthetic Example 1 according to the formulations shown in Table 5 wherein norbornane diisocyanate (NBDI) was used in place of HDI in Synthetic Example 1.

TABLE 5

| Synthetic Example | NBDI (g) | HMDI (g) | M400 (g) | Degree of Polymerization (n) | NBDI:HMDI (Molar Ratio) |
|---|---|---|---|---|---|
| 21 | 2062 | 262 | 2200 | 3 | 10:1 |
| 22 | 1031 | 262 | 800 | 4 | 5:1 |
| 23 | 619 | 262 | 800 | 3 | 3:1 |
| 24 | 206 | 262 | 800 | 1 | 1:1 |
| 25 | 206 | 262 | 400 | 3 | 1:1 |

Synthetic Examples 26 to 30

Carbodiimide compounds of Synthetic Examples 26 to 30 were prepared under the same conditions as in Synthetic Example 1 according to the formulations shown in Table 6 wherein isophorone diisocyanate (IPDI) was used in place of HMDI in Synthetic Example 1.

TABLE 6

| Synthetic Example | HDI (g) | IPDI (g) | M400 (g) | Degree of Polymerization (n) | HDI:IPDI (Molar Ratio) |
|---|---|---|---|---|---|
| 26 | 1682 | 222 | 2200 | 3 | 10:1 |
| 27 | 841 | 222 | 800 | 4 | 5:1 |
| 28 | 505 | 222 | 800 | 3 | 3:1 |
| 29 | 168 | 222 | 800 | 1 | 1:1 |
| 30 | 168 | 222 | 400 | 3 | 1:1 |

Synthetic Examples 31 to 35

Carbodiimide compounds of Synthetic Examples 31 to 35 were prepared under the same conditions as in Synthetic Example 6 according to the formulations shown in Table 7 wherein IPDI was used in place of HMDI in Synthetic Example 6.

TABLE 7

| Synthetic Example | $H_6$XDI (g) | IPDI (g) | M400 (g) | Degree of Polymerization (n) | $H_6$XDI:IPDI (Molar Ratio) |
|---|---|---|---|---|---|
| 31 | 1942 | 222 | 2200 | 3 | 10:1 |
| 32 | 971 | 222 | 800 | 4 | 5:1 |
| 33 | 583 | 222 | 800 | 3 | 3:1 |
| 34 | 194 | 222 | 800 | 1 | 1:1 |
| 35 | 194 | 222 | 400 | 3 | 1:1 |

Synthetic Examples 36 to 40

Carbodiimide compounds of Synthetic Examples 36 to 40 were prepared under the same conditions as in Synthetic Example 11 according to the formulations shown in Table 8 wherein IPDI was used in place of HMDI in Synthetic Example 11.

TABLE 8

| Syntheic Example | XDI (g) | IPDI (g) | M400 (g) | Degree of Polymerization (n) | XDI:IPDI (Molar Ratio) |
|---|---|---|---|---|---|
| 36 | 1882 | 222 | 2200 | 3 | 10:1 |
| 37 | 941 | 222 | 800 | 4 | 5:1 |
| 38 | 565 | 222 | 800 | 3 | 3:1 |
| 39 | 188 | 222 | 800 | 1 | 1:1 |
| 40 | 188 | 222 | 400 | 3 | 1:1 |

Synthetic Examples 41 to 45

Carbodiimide compounds of Synthetic Examples 41 to 45 were prepared under the same conditions as in Synthetic Example 16 according to the formulations shown in Table 9 wherein IPDI was used in place of HMDI in Synthetic Example 16.

TABLE 9

| Synthetic Example | TMHDI (g) | IPDI (g) | M400 (g) | Degree of Polymerization (n) | TMHDI:IPDI (Molar Ratio) |
|---|---|---|---|---|---|
| 41 | 2100 | 222 | 2200 | 3 | 10:1 |
| 42 | 1050 | 222 | 800 | 4 | 5:1 |
| 43 | 630 | 222 | 800 | 3 | 3:1 |
| 44 | 210 | 222 | 800 | 1 | 1:1 |
| 45 | 210 | 222 | 400 | 3 | 1:1 |

Synthetic Examples 46 to 50

Carbodiimide compounds of Synthetic Examples 46 to 50 were prepared under the same conditions as in Synthetic Example 21 according to the formulations shown in Table 10 wherein IPDI was used in place of HMDI in Synthetic Example 21.

TABLE 10

| Syntheic Example | NBDI (g) | IPDI (g) | M400 (g) | Degree of Polymerization (n) | NBDI:IPDI (Molar Ratio) |
|---|---|---|---|---|---|
| 46 | 2062 | 222 | 2200 | 3 | 10:1 |
| 47 | 1031 | 222 | 800 | 4 | 5:1 |
| 48 | 619 | 222 | 800 | 3 | 3:1 |
| 49 | 206 | 222 | 800 | 1 | 1:1 |
| 50 | 206 | 222 | 400 | 3 | 1:1 |

Synthetic Examples 51 to 55

Carbodiimide compounds of Synthetic Examples 51 to 55 were prepared under the same conditions as in Synthetic Example 1 according to the formulations shown in Table 11 wherein TMXDI was used in place of HMDI in Synthetic Example 1.

TABLE 11

| Synthetic Example | HDI (g) | TMXDI (g) | M400 (g) | Degree of Polymerization (n) | HDI:TMXDI (Molar Ratio) |
|---|---|---|---|---|---|
| 51 | 1682 | 244 | 2200 | 3 | 10:1 |
| 52 | 841 | 244 | 800 | 4 | 5:1 |
| 53 | 505 | 244 | 800 | 3 | 3:1 |
| 54 | 168 | 244 | 800 | 1 | 1:1 |
| 55 | 168 | 244 | 400 | 3 | 1:1 |

Synthetic Examples 56 to 60

Carbodiimide compounds of Synthetic Examples 56 to 60 were prepared under the same conditions as in Synthetic Example 6 according to the formulations shown in Table 12 wherein TMXDI was used in place of HMDI in Synthetic Example 6.

TABLE 12

| Synthetic Example | $H_6XDI$ (g) | TMXDI (g) | M400 (g) | Degree of Polymerization (n) | $H_6XDI$:TMXDI (Molar Ratio) |
|---|---|---|---|---|---|
| 56 | 1942 | 244 | 2200 | 3 | 10:1 |
| 57 | 971 | 244 | 800 | 4 | 5:1 |
| 58 | 583 | 244 | 800 | 3 | 3:1 |
| 59 | 194 | 244 | 800 | 1 | 1:1 |
| 60 | 194 | 244 | 400 | 3 | 1:1 |

Synthetic Examples 61 to 65

Carbodiimide compounds of Synthetic Examples 61 to 65 were prepared under the same conditions as in Synthetic Example 11 according to the formulations shown in Table 13 wherein TMXDI was used in place of HMDI in Synthetic Example 11.

TABLE 13

| Synthetic Example | XDI (g) | TMXDI (g) | M400 (g) | Degree of Polymerization (n) | XDI:TMXDI (Molar Ratio) |
|---|---|---|---|---|---|
| 61 | 1882 | 244 | 2200 | 3 | 10:1 |
| 62 | 941 | 244 | 800 | 4 | 5:1 |
| 63 | 565 | 244 | 800 | 3 | 3:1 |
| 64 | 188 | 244 | 800 | 1 | 1:1 |
| 65 | 188 | 244 | 400 | 3 | 1:1 |

Synthetic Examples 66 to 70

Carbodiimide compounds of Synthetic Examples 66 to 70 were prepared under the same conditions as in Synthetic Example 16 according to the formulations shown in Table 14 wherein TMXDI was used in place of HMDI in Synthetic Example 16.

TABLE 14

| Synthetic Example | TMHDI (g) | TMXDI (g) | M400 (g) | Degree of Polymerization (n) | TMHDI:TMXDI (Molar Ratio) |
|---|---|---|---|---|---|
| 66 | 2100 | 244 | 2200 | 3 | 10:1 |
| 67 | 1050 | 244 | 800 | 4 | 5:1 |
| 68 | 630 | 244 | 800 | 3 | 3:1 |
| 69 | 210 | 244 | 800 | 1 | 1:1 |
| 70 | 210 | 244 | 400 | 3 | 1:1 |

Synthetic Examples 71 to 75

Carbodiimide compounds of Synthetic Examples 71 to 75 were prepared under the same conditions as in Synthetic Example 21 according to the formulations shown in Table 15 wherein TMXDI was used in place of HMDI in Synthetic Example 21.

TABLE 15

| Synthetic Example | | NBDI (g) | TMXDI (g) | M400 (g) | Degree of Polymerization (n) | NBDI:TMXDI (Molar Ratio) |
|---|---|---|---|---|---|---|
| Synthetic | 71 | 2062 | 244 | 2200 | 3 | 10:1 |
| Example | 72 | 1031 | 244 | 800 | 4 | 5:1 |
| | 73 | 619 | 244 | 800 | 3 | 3:1 |
| | 74 | 206 | 244 | 800 | 1 | 1:1 |
| | 75 | 206 | 244 | 400 | 3 | 1:1 |

Synthetic Example 76

As shown in Table 16, 1048 g of HMDI and 10.5 g (1 wt % based on the total of the isocyanates) of a catalyst for carbodiimidization (3-methyl-1-phenyl-2-phosphorene-1-oxide) were charged in a 5000 ml reaction vessel equipped with a reflux condenser and an agitator, followed by agitation in a stream of nitrogen at 185° C. for 10 hours. The reaction vessel was allowed to cool down to 120 ° C., to which 800 g of M400 was added, followed by reaction for 1 hour while agitating at the same temperature, and again heating to 150° C., at which the reaction was caused to proceed for 5 hours under agitation. The completion of reaction was judged by measurement of infrared (IR) absorption spectra, through which an absorption of the isocyanate group at a wavelength of 2200 to 2300 cm$^{-1}$ was confirmed to disappear.

After the completion of the reaction, the reaction system was allowed to cool down to 60° C., to which distilled water was added so that the resin solid component was at a level of 2442 g (40 wt %), thereby obtaining a carbodiimide compound of Synthetic Example 76.

Synthetic Examples 77 to 81

Carbodiimide compounds of Synthetic Examples 77 to 81 were prepared under the same conditions as in Synthetic Example 76 according to the formulations shown in Table 16.

TABLE 16

| | HMDI (g) | TMXDI (g) | IPDI (g) | M400 (g) | Degree of Polymerization (n) | Amount of Catalyst (g) |
|---|---|---|---|---|---|---|
| Synthetic Example | | | | | | |
| 76 | 1048 | | | 800 | 3 | 10.5 |
| 77 | 1572 | | | 800 | 5 | 15.7 |
| 78 | | 976 | | 800 | 3 | 19.5 |
| 79 | | 1952 | | 800 | 7 | 39.0 |
| 80 | | | 888 | 800 | 3 | 8.9 |
| 81 | | | 1332 | 800 | 5 | 13.3 |

Synthetic Example 82

As shown in Table 17, 673 g of HDI and 800 g of M400 were charged into a 5 liters reaction vessel equipped with a reflux condenser and an agitator, and agitated at 120° C. for 1 hour under mechanical agitation. Moreover, 13.5 g (2 wt % based on the total of the isocyanates) of a catalyst for carbodiimidization (3-methyl-1-phenyl-2-phosphorene-1-oxide) were added to the mixture, followed by agitation in a stream of nitrogen at 185° C. for further 5 hours. The completion of the reaction was judged by the measurement of infrared (IR) absorption spectra, through which an absorption of the isocyanate group at a wavelength of 2200 to 2300 cm$^{-1}$ was confirmed to disappear.

After the completion of the reaction, the reaction system was allowed to cool down to 60° C., to which distilled water was added so that the resin solid component was at a level of 2011 g (40 wt %), thereby obtaining a carbodiimide compound of Synthetic Example 82.

Synthetic Examples 83 to 89

Carbodiimide compounds of Synthetic Examples 83 to 89 were prepared under the same conditions as in Synthetic Example 82 according to the formulations shown in Table 17.

TABLE 17

| | HDI (g) | H$_6$XDI (g) | XDI (g) | NBDI (g) | M400 (g) | Degree of Polymerization (n) | Amount of Catalyst (g) |
|---|---|---|---|---|---|---|---|
| Synthetic Example | | | | | | | |
| 82 | 673 | | | | 800 | 3 | 13.5 |
| 83 | 1008 | | | | 800 | 5 | 20.2 |
| 84 | | 777 | | | 800 | 3 | 15.5 |
| 85 | | 1165 | | | 800 | 5 | 23.3 |
| 86 | | | 753 | | 800 | 3 | 15.1 |
| 87 | | | 1129 | | 800 | 5 | 22.6 |
| 88 | | | | 824 | 800 | 3 | 16.5 |
| 89 | | | | 1236 | 800 | 5 | 24.7 |

Synthetic Example 90

As shown in Table 18, 696 g of TDI and 800 g of M400 were charged into a 5000 ml reaction vessel equipped with a reflux condenser and an agitator, and agitated at 50° C. for 1 hour under mechanical agitation, followed by addition of 7.0 g (1 wt % based on the total of the isocyanates) of a catalyst for carbodiimidization (3-methyl-1-phenyl-2-phosphorene-1-oxide) and agitation in a stream of nitrogen at 80° C. for further 5 hours. The completion of the reaction was judged by the measurement of infrared (IR) absorption spectra, through which an absorption of the isocyanate group at a wavelength of 2200 to 2300 cm$^{-1}$ was confirmed to disappear.

After the completion of the reaction, the reaction system was allowed to cool down to 60° C., to which distilled water was added so that the resin solid component was at a level of 2057 g (40 wt %), thereby preparing a carbodiimide compound of Synthetic Example 90.

Synthetic Examples 91 to 93

Carbodiimide compounds of Synthetic Examples 91 to 93 were prepared under the same conditions as in Synthetic Example 90 according to the formulations shown in Table 18.

TABLE 18

| | TDI (g) | MDI (g) | M400 (g) | Degree of Polymerization (n) | Amount of Catalyst (g) |
|---|---|---|---|---|---|
| Synthetic Example | | | | | |
| 90 | 696 | | 800 | 3 | 7.0 |
| 91 | 1044 | | 800 | 5 | 10.4 |
| 92 | | 1000 | 800 | 3 | 10.0 |
| 93 | | 1500 | 800 | 5 | 15.0 |

Example 1

Acrylic resin, Johncryl 511, (made by Johnson Polymer Co., Ltd.) was dissolved in distilled water to make a 10% resin aqueous solution. 10 parts by weight or 30 parts by weight of each of the carbodiimide compounds obtained in Synthetic Examples 1 to 93 as a solid matter was added to 1000 parts by weight (with 100 parts by weight of the solid matter) of the solution, and was well mixed under agitation. These solutions were, respectively, coated onto a polyethylene terephthalate (PET) film by means of a bar coater with a gap of 100 μm and crosslinked at 40° C. for 24 hours to provide test films Nos. 1 to 93.

Example 2

The general procedure of Example 1 was repeated except that an aqueous solution (containing 100 parts by weight of solid matter) of acrylic resin, Johncryl 734 (made by Johnson Polymer Co., Ltd.) was used, thereby obtaining test films.

Example 3

The general procedure of Example 1 was repeated except that an aqueous solution (containing 100 parts by weight of solid matter) of polyvinyl alcohol (PVA) resin, KL-318 (made by Kurare Co., Ltd.) was used, thereby obtaining test films.

Example 4

The general procedure of Example 1 was repeated except that an aqueous solution (containing 100 parts by weight of solid matter) of polyvinyl alcohol (PVA) resin, KM-118 (made by Kurare Co., Ltd.) was used, thereby obtaining test films.

Example 5

The general procedure of Example 1 was repeated except that an aqueous solution (containing 100 parts by weight of solid matter) of polyvinyl alcohol (PVA) resin, C-506 (made by Kurare Co., Ltd.) was used, thereby obtaining test films.

Comparative Examples 1 to 5

The general procedures of Examples 1 to 5 were, respectively, repeated without use of any carbodiimide compound, thereby obtaining test films of Comparative Examples 1 to 5, respectively.

Comparative Examples 6 to 10

10 parts by weight or 30 parts by weight of an epoxy crosslinking agent (Denacol EX-313, available from Nagase Chemical Ind. Co., Ltd.) was, respectively, added to the resin aqueous solutions of Examples 1 to 5, and well mixed under agitation, followed by coating on a PET film by use of a bar coater and crosslinking at 40° C. for 24 hours to obtain test films of Comparative Examples 6 to 10.

The test films of Examples 1 to 5 and Comparative Examples 1 to 10 were each subjected to a test for crosslinking effect under the following conditions. The results are shown in Tables 19 to 35.

Test for crosslinking effect

A: 0.28% aqueous ammonia

B: water/methanol=4/6

C: ethyl acetate

The respective cured films were each rubbed five times with absorbent cotton wetted with each of the solvents A to C, after which the thus rubbed film surface was judged through visual observation according to the following evaluation standards.

Evaluation standards

1: film dissolved

2: film marred slightly

3: no change in film

Example 6

Polyvinyl alcohol (PVA) resin KL-318 (Kurare Co., Ltd.) was dissolved in distilled water to prepare a 10% resin aqueous solution. 5 or 10 parts by weight, as a solid matter, of each of the carbodiimide compounds of Synthetic Examples 1 to 93 was added to 1000 parts by weight of the solution (100 parts by weight of the solid matter), followed by mixing well under agitation and coating onto a polyethylene terephthalate (PET) film by means of a bar coater with a gap of 100 μm. The resultant coatings were dried and cured at 40° C. for 24 hours to obtain test film Nos. 1 to 93.

Example 7

The general procedure of Example 6 was repeated using polyvinyl alcohol (PVA) resin KM-118 (Kurare Co., Ltd.), thereby obtaining a test film.

Example 8

The general procedure of Example 6 was repeated using polyvinyl alcohol (PVA) resin C-506 (Kurare Co., Ltd.), thereby obtaining a test film.

Comparative Examples 11 to 13

The general procedures of Examples 6 to 8 were repeated without addition of any carbodiimide compounds, thereby obtaining test films of Comparative Examples 11 to 13, respectively.

Comparative Examples 14 to 16

The general procedures of Examples 6 to 8 were repeated except that 5 or 10 parts by weight of an epoxy crosslinking agent (Denacol EX-313 of Nagase Chemical Ind. Co., Ltd.) was added to the respective resin aqueous solutions (100 parts by weight of the solid matter) in place of the carbodiimide compounds, thereby obtaining test films of Comparative Examples 14 to 16.

The test films of Examples 6 to 8 and Comparative Examples 11 to 16 were each subjected to a water resistance test under the following conditions. The results are shown in Tables 36 to 40.

Water resistance test

Each test film was cut into a piece having a size of 5 cm×10 cm and immersed in water of 20° C. for 24 hours, followed by visually observing any change of the piece and judging the change according to the following standards.

⊚: no change in or on film

◯: film clouded

Δ: film partly dissolved out x: film wholly dissolved out

TABLE 19

[Example 1]
(1) Acrylic resin Johncryl 511
A: 0.28% aqueous ammonia

| No. | 10 parts | 30 parts |
|---|---|---|
| 1 | 3 | 3 |
| 2 | 3 | 3 |
| 3 | 3 | 3 |
| 4 | 3 | 3 |
| 5 | 3 | 3 |
| 6 | 3 | 3 |
| 7 | 3 | 3 |
| 8 | 3 | 3 |
| 9 | 3 | 3 |
| 10 | 3 | 3 |
| 11 | 3 | 3 |
| 12 | 3 | 3 |
| 13 | 3 | 3 |
| 14 | 3 | 3 |
| 15 | 3 | 3 |
| 16 | 3 | 3 |
| 17 | 3 | 3 |
| 18 | 3 | 3 |
| 19 | 3 | 3 |
| 20 | 3 | 3 |
| 21 | 3 | 3 |
| 22 | 3 | 3 |
| 23 | 3 | 3 |
| 24 | 3 | 3 |
| 25 | 3 | 3 |
| 26 | 3 | 3 |
| 27 | 3 | 3 |
| 28 | 3 | 3 |
| 29 | 3 | 3 |
| 30 | 3 | 3 |
| 31 | 3 | 3 |
| 32 | 3 | 3 |
| 33 | 3 | 3 |
| 34 | 3 | 3 |
| 35 | 3 | 3 |
| 36 | 3 | 3 |

TABLE 19-continued

[Example 1]
(1) Acrylic resin Johncryl 511
A: 0.28% aqueous ammonia

| No. | 10 parts | 30 parts |
|---|---|---|
| 37 | 3 | 3 |
| 38 | 3 | 3 |
| 39 | 3 | 3 |
| 40 | 3 | 3 |
| 41 | 3 | 3 |
| 42 | 3 | 3 |
| 43 | 3 | 3 |
| 44 | 3 | 3 |
| 45 | 3 | 3 |
| 46 | 3 | 3 |
| 47 | 3 | 3 |
| 48 | 3 | 3 |
| 49 | 3 | 3 |
| 50 | 3 | 3 |
| 51 | 3 | 3 |
| 52 | 3 | 3 |
| 53 | 3 | 3 |
| 54 | 3 | 3 |
| 55 | 3 | 3 |
| 56 | 3 | 3 |
| 57 | 3 | 3 |
| 58 | 3 | 3 |
| 59 | 3 | 3 |
| 60 | 3 | 3 |
| 61 | 3 | 3 |
| 62 | 3 | 3 |
| 63 | 3 | 3 |
| 64 | 3 | 3 |
| 65 | 3 | 3 |
| 66 | 3 | 3 |
| 67 | 3 | 3 |
| 68 | 3 | 3 |
| 69 | 3 | 3 |
| 70 | 3 | 3 |
| 71 | 3 | 3 |
| 72 | 3 | 3 |
| 73 | 3 | 3 |
| 74 | 3 | 3 |
| 75 | 3 | 3 |
| 76 | 3 | 3 |
| 77 | 3 | 3 |
| 78 | 3 | 3 |
| 79 | 3 | 3 |
| 80 | 3 | 3 |
| 81 | 3 | 3 |
| 82 | 3 | 3 |
| 83 | 3 | 3 |
| 84 | 3 | 3 |
| 85 | 3 | 3 |
| 86 | 3 | 3 |
| 87 | 3 | 3 |
| 88 | 3 | 3 |
| 89 | 3 | 3 |
| 90 | 3 | 3 |
| 91 | 3 | 3 |
| 92 | 3 | 3 |
| 93 | 3 | 3 |

TABLE 20

[Example 1]
(1) Acrylic resin Johncryl 511
B: Water/methanol = 4/6

| No. | 10 parts | 30 parts |
|---|---|---|
| 1 | 3 | 3 |
| 2 | 3 | 3 |
| 3 | 3 | 3 |
| 4 | 3 | 3 |
| 5 | 3 | 3 |
| 6 | 3 | 3 |
| 7 | 3 | 3 |
| 8 | 3 | 3 |
| 9 | 3 | 3 |
| 10 | 3 | 3 |
| 11 | 3 | 3 |
| 12 | 3 | 3 |
| 13 | 3 | 3 |
| 14 | 3 | 3 |
| 15 | 3 | 3 |
| 16 | 3 | 3 |
| 17 | 3 | 3 |
| 18 | 3 | 3 |
| 19 | 3 | 3 |
| 20 | 3 | 3 |
| 21 | 3 | 3 |
| 22 | 3 | 3 |
| 23 | 3 | 3 |
| 24 | 3 | 3 |
| 25 | 3 | 3 |
| 26 | 3 | 3 |
| 27 | 3 | 3 |
| 28 | 3 | 3 |
| 29 | 3 | 3 |
| 30 | 3 | 3 |
| 31 | 3 | 3 |
| 32 | 3 | 3 |
| 33 | 3 | 3 |
| 34 | 3 | 3 |
| 35 | 3 | 3 |
| 36 | 3 | 3 |
| 37 | 3 | 3 |
| 38 | 3 | 3 |
| 39 | 3 | 3 |
| 40 | 3 | 3 |
| 41 | 3 | 3 |
| 42 | 3 | 3 |
| 43 | 3 | 3 |
| 44 | 3 | 3 |
| 45 | 3 | 3 |
| 46 | 3 | 3 |
| 47 | 3 | 3 |
| 48 | 3 | 3 |
| 49 | 3 | 3 |
| 50 | 3 | 3 |
| 51 | 3 | 3 |
| 52 | 3 | 3 |
| 53 | 3 | 3 |
| 54 | 3 | 3 |
| 55 | 3 | 3 |
| 56 | 3 | 3 |
| 57 | 3 | 3 |
| 58 | 3 | 3 |
| 59 | 3 | 3 |
| 60 | 3 | 3 |
| 61 | 3 | 3 |
| 62 | 3 | 3 |
| 63 | 3 | 3 |
| 64 | 3 | 3 |
| 65 | 3 | 3 |
| 66 | 3 | 3 |
| 67 | 3 | 3 |
| 68 | 3 | 3 |
| 69 | 3 | 3 |
| 70 | 3 | 3 |
| 71 | 3 | 3 |
| 72 | 3 | 3 |
| 73 | 3 | 3 |
| 74 | 3 | 3 |
| 75 | 3 | 3 |
| 76 | 3 | 3 |
| 77 | 3 | 3 |

TABLE 20-continued

[Example 1]
(1) Acrylic resin Johncryl 511
B: Water/methanol = 4/6

| No. | 10 parts | 30 parts |
| --- | --- | --- |
| 78 | 3 | 3 |
| 79 | 3 | 3 |
| 80 | 3 | 3 |
| 81 | 3 | 3 |
| 82 | 3 | 3 |
| 83 | 3 | 3 |
| 84 | 3 | 3 |
| 85 | 3 | 3 |
| 86 | 3 | 3 |
| 87 | 3 | 3 |
| 88 | 3 | 3 |
| 89 | 3 | 3 |
| 90 | 3 | 3 |
| 91 | 3 | 3 |
| 92 | 3 | 3 |
| 93 | 3 | 3 |

TABLE 21

[Example 1]
(1) Acrylic resin Johncryl 511
C: Ethyl acetate

| No. | 10 parts | 30 parts |
| --- | --- | --- |
| 1 | 3 | 3 |
| 2 | 3 | 3 |
| 3 | 3 | 3 |
| 4 | 3 | 3 |
| 5 | 3 | 3 |
| 6 | 3 | 3 |
| 7 | 3 | 3 |
| 8 | 3 | 3 |
| 9 | 3 | 3 |
| 10 | 3 | 3 |
| 11 | 3 | 3 |
| 12 | 3 | 3 |
| 13 | 3 | 3 |
| 14 | 3 | 3 |
| 15 | 3 | 3 |
| 16 | 3 | 3 |
| 17 | 3 | 3 |
| 18 | 3 | 3 |
| 19 | 3 | 3 |
| 20 | 3 | 3 |
| 21 | 3 | 3 |
| 22 | 3 | 3 |
| 23 | 3 | 3 |
| 24 | 3 | 3 |
| 25 | 3 | 3 |
| 26 | 3 | 3 |
| 27 | 3 | 3 |
| 28 | 3 | 3 |
| 29 | 3 | 3 |
| 30 | 3 | 3 |
| 31 | 3 | 3 |
| 32 | 3 | 3 |
| 33 | 3 | 3 |
| 34 | 3 | 3 |
| 35 | 3 | 3 |
| 36 | 3 | 3 |
| 37 | 3 | 3 |
| 38 | 3 | 3 |
| 39 | 3 | 3 |
| 40 | 3 | 3 |
| 41 | 3 | 3 |
| 42 | 3 | 3 |
| 43 | 3 | 3 |
| 44 | 3 | 3 |
| 45 | 3 | 3 |

TABLE 21-continued

[Example 1]
(1) Acrylic resin Johncryl 511
C: Ethyl acetate

| No. | 10 parts | 30 parts |
| --- | --- | --- |
| 46 | 3 | 3 |
| 47 | 3 | 3 |
| 48 | 3 | 3 |
| 49 | 3 | 3 |
| 50 | 3 | 3 |
| 51 | 3 | 3 |
| 52 | 3 | 3 |
| 53 | 3 | 3 |
| 54 | 3 | 3 |
| 55 | 3 | 3 |
| 56 | 3 | 3 |
| 57 | 3 | 3 |
| 58 | 3 | 3 |
| 59 | 3 | 3 |
| 60 | 3 | 3 |
| 61 | 3 | 3 |
| 62 | 3 | 3 |
| 63 | 3 | 3 |
| 64 | 3 | 3 |
| 65 | 3 | 3 |
| 66 | 3 | 3 |
| 67 | 3 | 3 |
| 68 | 3 | 3 |
| 69 | 3 | 3 |
| 70 | 3 | 3 |
| 71 | 3 | 3 |
| 72 | 3 | 3 |
| 73 | 3 | 3 |
| 74 | 3 | 3 |
| 75 | 3 | 3 |
| 76 | 3 | 3 |
| 77 | 3 | 3 |
| 78 | 3 | 3 |
| 79 | 3 | 3 |
| 80 | 3 | 3 |
| 81 | 3 | 3 |
| 82 | 3 | 3 |
| 83 | 3 | 3 |
| 84 | 3 | 3 |
| 85 | 3 | 3 |
| 86 | 3 | 3 |
| 87 | 3 | 3 |
| 88 | 3 | 3 |
| 89 | 3 | 3 |
| 90 | 3 | 3 |
| 91 | 3 | 3 |
| 92 | 3 | 3 |
| 93 | 3 | 3 |

TABLE 22

[Example 2]
(2) Acrylic resin Johncryl 734
A: 0.28% aqueous ammonia

| No. | 10 parts | 30 parts |
| --- | --- | --- |
| 1 | 3 | 3 |
| 2 | 3 | 3 |
| 3 | 3 | 3 |
| 4 | 3 | 3 |
| 5 | 3 | 3 |
| 6 | 3 | 3 |
| 7 | 3 | 3 |
| 8 | 3 | 3 |
| 9 | 3 | 3 |
| 10 | 3 | 3 |
| 11 | 3 | 3 |
| 12 | 3 | 3 |
| 13 | 3 | 3 |

TABLE 22-continued

[Example 2]
(2) Acrylic resin Johncryl 734
A: 0.28% aqueous ammonia

| No. | 10 parts | 30 parts |
|---|---|---|
| 14 | 3 | 3 |
| 15 | 3 | 3 |
| 16 | 3 | 3 |
| 17 | 3 | 3 |
| 18 | 3 | 3 |
| 19 | 3 | 3 |
| 20 | 3 | 3 |
| 21 | 3 | 3 |
| 22 | 3 | 3 |
| 23 | 3 | 3 |
| 24 | 3 | 3 |
| 25 | 3 | 3 |
| 26 | 3 | 3 |
| 27 | 3 | 3 |
| 28 | 3 | 3 |
| 29 | 3 | 3 |
| 30 | 3 | 3 |
| 31 | 3 | 3 |
| 32 | 3 | 3 |
| 33 | 3 | 3 |
| 34 | 3 | 3 |
| 35 | 3 | 3 |
| 36 | 3 | 3 |
| 37 | 3 | 3 |
| 38 | 3 | 3 |
| 39 | 3 | 3 |
| 40 | 3 | 3 |
| 41 | 3 | 3 |
| 42 | 3 | 3 |
| 43 | 3 | 3 |
| 44 | 3 | 3 |
| 45 | 3 | 3 |
| 46 | 3 | 3 |
| 47 | 3 | 3 |
| 48 | 3 | 3 |
| 49 | 3 | 3 |
| 50 | 3 | 3 |
| 51 | 3 | 3 |
| 52 | 3 | 3 |
| 53 | 3 | 3 |
| 54 | 3 | 3 |
| 55 | 3 | 3 |
| 56 | 3 | 3 |
| 57 | 3 | 3 |
| 58 | 3 | 3 |
| 59 | 3 | 3 |
| 60 | 3 | 3 |
| 61 | 3 | 3 |
| 62 | 3 | 3 |
| 63 | 3 | 3 |
| 64 | 3 | 3 |
| 65 | 3 | 3 |
| 66 | 3 | 3 |
| 67 | 3 | 3 |
| 68 | 3 | 3 |
| 69 | 3 | 3 |
| 70 | 3 | 3 |
| 71 | 3 | 3 |
| 72 | 3 | 3 |
| 73 | 3 | 3 |
| 74 | 3 | 3 |
| 75 | 3 | 3 |
| 76 | 3 | 3 |
| 77 | 3 | 3 |
| 78 | 3 | 3 |
| 79 | 3 | 3 |
| 80 | 3 | 3 |
| 81 | 3 | 3 |
| 82 | 3 | 3 |
| 83 | 3 | 3 |
| 84 | 3 | 3 |
| 85 | 3 | 3 |
| 86 | 3 | 3 |
| 87 | 3 | 3 |
| 88 | 3 | 3 |
| 89 | 3 | 3 |
| 90 | 3 | 3 |
| 91 | 3 | 3 |
| 92 | 3 | 3 |
| 93 | 3 | 3 |

TABLE 23

[Example 2]
(2) Acrylic resin Johncryl 734
B: Water/methanol = 4/6

| No. | 10 parts | 30 parts |
|---|---|---|
| 1 | 3 | 3 |
| 2 | 3 | 3 |
| 3 | 3 | 3 |
| 4 | 3 | 3 |
| 5 | 3 | 3 |
| 6 | 3 | 3 |
| 7 | 3 | 3 |
| 8 | 3 | 3 |
| 9 | 3 | 3 |
| 10 | 3 | 3 |
| 11 | 3 | 3 |
| 12 | 3 | 3 |
| 13 | 3 | 3 |
| 14 | 3 | 3 |
| 15 | 3 | 3 |
| 16 | 3 | 3 |
| 17 | 3 | 3 |
| 18 | 3 | 3 |
| 19 | 3 | 3 |
| 20 | 3 | 3 |
| 21 | 3 | 3 |
| 22 | 3 | 3 |
| 23 | 3 | 3 |
| 24 | 3 | 3 |
| 25 | 3 | 3 |
| 26 | 3 | 3 |
| 27 | 3 | 3 |
| 28 | 3 | 3 |
| 29 | 3 | 3 |
| 30 | 3 | 3 |
| 31 | 3 | 3 |
| 32 | 3 | 3 |
| 33 | 3 | 3 |
| 34 | 3 | 3 |
| 35 | 3 | 3 |
| 36 | 3 | 3 |
| 37 | 3 | 3 |
| 38 | 3 | 3 |
| 39 | 3 | 3 |
| 40 | 3 | 3 |
| 41 | 3 | 3 |
| 42 | 3 | 3 |
| 43 | 3 | 3 |
| 44 | 3 | 3 |
| 45 | 3 | 3 |
| 46 | 3 | 3 |
| 47 | 3 | 3 |
| 48 | 3 | 3 |
| 49 | 3 | 3 |
| 50 | 3 | 3 |
| 51 | 3 | 3 |
| 52 | 3 | 3 |
| 53 | 3 | 3 |
| 54 | 3 | 3 |

TABLE 23-continued

[Example 2]
(2) Acrylic resin Johncryl 734
B: Water/methanol = 4/6

| No. | 10 parts | 30 parts |
|---|---|---|
| 55 | 3 | 3 |
| 56 | 3 | 3 |
| 57 | 3 | 3 |
| 58 | 3 | 3 |
| 59 | 3 | 3 |
| 60 | 3 | 3 |
| 61 | 3 | 3 |
| 62 | 3 | 3 |
| 63 | 3 | 3 |
| 64 | 3 | 3 |
| 65 | 3 | 3 |
| 66 | 3 | 3 |
| 67 | 3 | 3 |
| 68 | 3 | 3 |
| 69 | 3 | 3 |
| 70 | 3 | 3 |
| 71 | 3 | 3 |
| 72 | 3 | 3 |
| 73 | 3 | 3 |
| 74 | 3 | 3 |
| 75 | 3 | 3 |
| 76 | 3 | 3 |
| 77 | 3 | 3 |
| 78 | 3 | 3 |
| 79 | 3 | 3 |
| 80 | 3 | 3 |
| 81 | 3 | 3 |
| 82 | 3 | 3 |
| 83 | 3 | 3 |
| 84 | 3 | 3 |
| 85 | 3 | 3 |
| 86 | 3 | 3 |
| 87 | 3 | 3 |
| 88 | 3 | 3 |
| 89 | 3 | 3 |
| 90 | 3 | 3 |
| 91 | 3 | 3 |
| 92 | 3 | 3 |
| 93 | 3 | 3 |

TABLE 24

[Example 2]
(2) Acrylic resin Johncryl 734
C: Ethyl acetate

| No. | 10 parts | 30 parts |
|---|---|---|
| 1 | 3 | 3 |
| 2 | 3 | 3 |
| 3 | 3 | 3 |
| 4 | 3 | 3 |
| 5 | 3 | 3 |
| 6 | 3 | 3 |
| 7 | 3 | 3 |
| 8 | 3 | 3 |
| 9 | 3 | 3 |
| 10 | 3 | 3 |
| 11 | 3 | 3 |
| 12 | 3 | 3 |
| 13 | 3 | 3 |
| 14 | 3 | 3 |
| 15 | 3 | 3 |
| 16 | 3 | 3 |
| 17 | 3 | 3 |
| 18 | 3 | 3 |
| 19 | 3 | 3 |
| 20 | 3 | 3 |
| 21 | 3 | 3 |
| 22 | 3 | 3 |
| 23 | 3 | 3 |
| 24 | 3 | 3 |
| 25 | 3 | 3 |
| 26 | 3 | 3 |
| 27 | 3 | 3 |
| 28 | 3 | 3 |
| 29 | 3 | 3 |
| 30 | 3 | 3 |
| 31 | 3 | 3 |
| 32 | 3 | 3 |
| 33 | 3 | 3 |
| 34 | 3 | 3 |
| 35 | 3 | 3 |
| 36 | 3 | 3 |
| 37 | 3 | 3 |
| 38 | 3 | 3 |
| 39 | 3 | 3 |
| 40 | 3 | 3 |
| 41 | 3 | 3 |
| 42 | 3 | 3 |
| 43 | 3 | 3 |
| 44 | 3 | 3 |
| 45 | 3 | 3 |
| 46 | 3 | 3 |
| 47 | 3 | 3 |
| 48 | 3 | 3 |
| 49 | 3 | 3 |
| 50 | 3 | 3 |
| 51 | 3 | 3 |
| 52 | 3 | 3 |
| 53 | 3 | 3 |
| 54 | 3 | 3 |
| 55 | 3 | 3 |
| 56 | 3 | 3 |
| 57 | 3 | 3 |
| 58 | 3 | 3 |
| 59 | 3 | 3 |
| 60 | 3 | 3 |
| 61 | 3 | 3 |
| 62 | 3 | 3 |
| 63 | 3 | 3 |
| 64 | 3 | 3 |
| 65 | 3 | 3 |
| 66 | 3 | 3 |
| 67 | 3 | 3 |
| 68 | 3 | 3 |
| 69 | 3 | 3 |
| 70 | 3 | 3 |
| 71 | 3 | 3 |
| 72 | 3 | 3 |
| 73 | 3 | 3 |
| 74 | 3 | 3 |
| 75 | 3 | 3 |
| 76 | 3 | 3 |
| 77 | 3 | 3 |
| 78 | 3 | 3 |
| 79 | 3 | 3 |
| 80 | 3 | 3 |
| 81 | 3 | 3 |
| 82 | 3 | 3 |
| 83 | 3 | 3 |
| 84 | 3 | 3 |
| 85 | 3 | 3 |
| 86 | 3 | 3 |
| 87 | 3 | 3 |
| 88 | 3 | 3 |
| 89 | 3 | 3 |
| 90 | 3 | 3 |
| 91 | 3 | 3 |
| 92 | 3 | 3 |
| 93 | 3 | 3 |

TABLE 25

[Example 3]
(3) PVA resin KL-318
A: 0.28% aqueous ammonia

| No. | 10 parts | 30 parts |
|---|---|---|
| 1 | 3 | 3 |
| 2 | 3 | 3 |
| 3 | 3 | 3 |
| 4 | 3 | 3 |
| 5 | 3 | 3 |
| 6 | 3 | 3 |
| 7 | 3 | 3 |
| 8 | 3 | 3 |
| 9 | 3 | 3 |
| 10 | 3 | 3 |
| 11 | 3 | 3 |
| 12 | 3 | 3 |
| 13 | 3 | 3 |
| 14 | 3 | 3 |
| 15 | 3 | 3 |
| 16 | 3 | 3 |
| 17 | 3 | 3 |
| 18 | 3 | 3 |
| 19 | 3 | 3 |
| 20 | 3 | 3 |
| 21 | 3 | 3 |
| 22 | 3 | 3 |
| 23 | 3 | 3 |
| 24 | 3 | 3 |
| 25 | 3 | 3 |
| 26 | 3 | 3 |
| 27 | 3 | 3 |
| 28 | 3 | 3 |
| 29 | 3 | 3 |
| 30 | 3 | 3 |
| 31 | 3 | 3 |
| 32 | 3 | 3 |
| 33 | 3 | 3 |
| 34 | 3 | 3 |
| 35 | 3 | 3 |
| 36 | 3 | 3 |
| 37 | 3 | 3 |
| 38 | 3 | 3 |
| 39 | 3 | 3 |
| 40 | 3 | 3 |
| 41 | 3 | 3 |
| 42 | 3 | 3 |
| 43 | 3 | 3 |
| 44 | 3 | 3 |
| 45 | 3 | 3 |
| 46 | 3 | 3 |
| 47 | 3 | 3 |
| 48 | 3 | 3 |
| 49 | 3 | 3 |
| 50 | 3 | 3 |
| 51 | 3 | 3 |
| 52 | 3 | 3 |
| 53 | 3 | 3 |
| 54 | 3 | 3 |
| 55 | 3 | 3 |
| 56 | 3 | 3 |
| 57 | 3 | 3 |
| 58 | 3 | 3 |
| 59 | 3 | 3 |
| 60 | 3 | 3 |
| 61 | 3 | 3 |
| 62 | 3 | 3 |
| 63 | 3 | 3 |
| 64 | 3 | 3 |
| 65 | 3 | 3 |
| 66 | 3 | 3 |
| 67 | 3 | 3 |
| 68 | 3 | 3 |
| 69 | 3 | 3 |
| 70 | 3 | 3 |
| 71 | 3 | 3 |
| 72 | 3 | 3 |
| 73 | 3 | 3 |
| 74 | 3 | 3 |
| 75 | 3 | 3 |
| 76 | 3 | 3 |
| 77 | 3 | 3 |
| 78 | 3 | 3 |
| 79 | 3 | 3 |
| 80 | 3 | 3 |
| 81 | 3 | 3 |
| 82 | 3 | 3 |
| 83 | 3 | 3 |
| 84 | 3 | 3 |
| 85 | 3 | 3 |
| 86 | 3 | 3 |
| 87 | 3 | 3 |
| 88 | 3 | 3 |
| 89 | 3 | 3 |
| 90 | 3 | 3 |
| 91 | 3 | 3 |
| 92 | 3 | 3 |
| 93 | 3 | 3 |

TABLE 26

[Example 3]
(3) PVA resin KL-318
B: Water/methanol = 4/6

| No. | 10 parts | 30 parts |
|---|---|---|
| 1 | 3 | 3 |
| 2 | 3 | 3 |
| 3 | 3 | 3 |
| 4 | 3 | 3 |
| 5 | 3 | 3 |
| 6 | 3 | 3 |
| 7 | 3 | 3 |
| 8 | 3 | 3 |
| 9 | 3 | 3 |
| 10 | 3 | 3 |
| 11 | 3 | 3 |
| 12 | 3 | 3 |
| 13 | 3 | 3 |
| 14 | 3 | 3 |
| 15 | 3 | 3 |
| 16 | 3 | 3 |
| 17 | 3 | 3 |
| 18 | 3 | 3 |
| 19 | 3 | 3 |
| 20 | 3 | 3 |
| 21 | 3 | 3 |
| 22 | 3 | 3 |
| 23 | 3 | 3 |
| 24 | 3 | 3 |
| 25 | 3 | 3 |
| 26 | 3 | 3 |
| 27 | 3 | 3 |
| 28 | 3 | 3 |
| 29 | 3 | 3 |
| 30 | 3 | 3 |
| 31 | 3 | 3 |
| 32 | 3 | 3 |
| 33 | 3 | 3 |
| 34 | 3 | 3 |
| 35 | 3 | 3 |
| 36 | 3 | 3 |
| 37 | 3 | 3 |
| 38 | 3 | 3 |
| 39 | 3 | 3 |
| 40 | 3 | 3 |
| 41 | 3 | 3 |

TABLE 26-continued

[Example 3]
(3) PVA resin KL-318
B: Water/methanol = 4/6

| No. | 10 parts | 30 parts |
|-----|----------|----------|
| 42 | 3 | 3 |
| 43 | 3 | 3 |
| 44 | 3 | 3 |
| 45 | 3 | 3 |
| 46 | 3 | 3 |
| 47 | 3 | 3 |
| 48 | 3 | 3 |
| 49 | 3 | 3 |
| 50 | 3 | 3 |
| 51 | 3 | 3 |
| 52 | 3 | 3 |
| 53 | 3 | 3 |
| 54 | 3 | 3 |
| 55 | 3 | 3 |
| 56 | 3 | 3 |
| 57 | 3 | 3 |
| 58 | 3 | 3 |
| 59 | 3 | 3 |
| 60 | 3 | 3 |
| 61 | 3 | 3 |
| 62 | 3 | 3 |
| 63 | 3 | 3 |
| 64 | 3 | 3 |
| 65 | 3 | 3 |
| 66 | 3 | 3 |
| 67 | 3 | 3 |
| 68 | 3 | 3 |
| 69 | 3 | 3 |
| 70 | 3 | 3 |
| 71 | 3 | 3 |
| 72 | 3 | 3 |
| 73 | 3 | 3 |
| 74 | 3 | 3 |
| 75 | 3 | 3 |
| 76 | 3 | 3 |
| 77 | 3 | 3 |
| 78 | 3 | 3 |
| 79 | 3 | 3 |
| 80 | 3 | 3 |
| 81 | 3 | 3 |
| 82 | 3 | 3 |
| 83 | 3 | 3 |
| 84 | 3 | 3 |
| 85 | 3 | 3 |
| 86 | 3 | 3 |
| 87 | 3 | 3 |
| 88 | 3 | 3 |
| 89 | 3 | 3 |
| 90 | 3 | 3 |
| 91 | 3 | 3 |
| 92 | 3 | 3 |
| 93 | 3 | 3 |

TABLE 27

[Example 3]
(3) PVA resin KL-318
C: Ethyl acetate

| No. | 10 parts | 30 parts |
|-----|----------|----------|
| 1 | 3 | 3 |
| 2 | 3 | 3 |
| 3 | 3 | 3 |
| 4 | 3 | 3 |
| 5 | 3 | 3 |
| 6 | 3 | 3 |
| 7 | 3 | 3 |
| 8 | 3 | 3 |
| 9 | 3 | 3 |
| 10 | 3 | 3 |
| 11 | 3 | 3 |
| 12 | 3 | 3 |
| 13 | 3 | 3 |
| 14 | 3 | 3 |
| 15 | 3 | 3 |
| 16 | 3 | 3 |
| 17 | 3 | 3 |
| 18 | 3 | 3 |
| 19 | 3 | 3 |
| 20 | 3 | 3 |
| 21 | 3 | 3 |
| 22 | 3 | 3 |
| 23 | 3 | 3 |
| 24 | 3 | 3 |
| 25 | 3 | 3 |
| 26 | 3 | 3 |
| 27 | 3 | 3 |
| 28 | 3 | 3 |
| 29 | 3 | 3 |
| 30 | 3 | 3 |
| 31 | 3 | 3 |
| 32 | 3 | 3 |
| 33 | 3 | 3 |
| 34 | 3 | 3 |
| 35 | 3 | 3 |
| 36 | 3 | 3 |
| 37 | 3 | 3 |
| 38 | 3 | 3 |
| 39 | 3 | 3 |
| 40 | 3 | 3 |
| 41 | 3 | 3 |
| 42 | 3 | 3 |
| 43 | 3 | 3 |
| 44 | 3 | 3 |
| 45 | 3 | 3 |
| 46 | 3 | 3 |
| 47 | 3 | 3 |
| 48 | 3 | 3 |
| 49 | 3 | 3 |
| 50 | 3 | 3 |
| 51 | 3 | 3 |
| 52 | 3 | 3 |
| 53 | 3 | 3 |
| 54 | 3 | 3 |
| 55 | 3 | 3 |
| 56 | 3 | 3 |
| 57 | 3 | 3 |
| 58 | 3 | 3 |
| 59 | 3 | 3 |
| 60 | 3 | 3 |
| 61 | 3 | 3 |
| 62 | 3 | 3 |
| 63 | 3 | 3 |
| 64 | 3 | 3 |
| 65 | 3 | 3 |
| 66 | 3 | 3 |
| 67 | 3 | 3 |
| 68 | 3 | 3 |
| 69 | 3 | 3 |
| 70 | 3 | 3 |
| 71 | 3 | 3 |
| 72 | 3 | 3 |
| 73 | 3 | 3 |
| 74 | 3 | 3 |
| 75 | 3 | 3 |
| 76 | 3 | 3 |
| 77 | 3 | 3 |
| 78 | 3 | 3 |
| 79 | 3 | 3 |
| 80 | 3 | 3 |
| 81 | 3 | 3 |
| 82 | 3 | 3 |

TABLE 27-continued

[Example 3]
(3) PVA resin KL-318
C: Ethyl acetate

| No. | 10 parts | 30 parts |
|-----|----------|----------|
| 83 | 3 | 3 |
| 84 | 3 | 3 |
| 85 | 3 | 3 |
| 86 | 3 | 3 |
| 87 | 3 | 3 |
| 88 | 3 | 3 |
| 89 | 3 | 3 |
| 90 | 3 | 3 |
| 91 | 3 | 3 |
| 92 | 3 | 3 |
| 93 | 3 | 3 |

TABLE 28

[Example 4]
(4) PVA resin KM-118
A: 0.28% aqueous ammonia

| No. | 10 parts | 30 parts |
|-----|----------|----------|
| 1 | 3 | 3 |
| 2 | 3 | 3 |
| 3 | 3 | 3 |
| 4 | 3 | 3 |
| 5 | 3 | 3 |
| 6 | 3 | 3 |
| 7 | 3 | 3 |
| 8 | 3 | 3 |
| 9 | 3 | 3 |
| 10 | 3 | 3 |
| 11 | 3 | 3 |
| 12 | 3 | 3 |
| 13 | 3 | 3 |
| 14 | 3 | 3 |
| 15 | 3 | 3 |
| 16 | 3 | 3 |
| 17 | 3 | 3 |
| 18 | 3 | 3 |
| 19 | 3 | 3 |
| 20 | 3 | 3 |
| 21 | 3 | 3 |
| 22 | 3 | 3 |
| 23 | 3 | 3 |
| 24 | 3 | 3 |
| 25 | 3 | 3 |
| 26 | 3 | 3 |
| 27 | 3 | 3 |
| 28 | 3 | 3 |
| 29 | 3 | 3 |
| 30 | 3 | 3 |
| 31 | 3 | 3 |
| 32 | 3 | 3 |
| 33 | 3 | 3 |
| 34 | 3 | 3 |
| 35 | 3 | 3 |
| 36 | 3 | 3 |
| 37 | 3 | 3 |
| 38 | 3 | 3 |
| 39 | 3 | 3 |
| 40 | 3 | 3 |
| 41 | 3 | 3 |
| 42 | 3 | 3 |
| 43 | 3 | 3 |
| 44 | 3 | 3 |
| 45 | 3 | 3 |
| 46 | 3 | 3 |
| 47 | 3 | 3 |
| 48 | 3 | 3 |
| 49 | 3 | 3 |
| 50 | 3 | 3 |

TABLE 28-continued

[Example 4]
(4) PVA resin KM-118
A: 0.28% aqueous ammonia

| No. | 10 parts | 30 parts |
|-----|----------|----------|
| 51 | 3 | 3 |
| 52 | 3 | 3 |
| 53 | 3 | 3 |
| 54 | 3 | 3 |
| 55 | 3 | 3 |
| 56 | 3 | 3 |
| 57 | 3 | 3 |
| 58 | 3 | 3 |
| 59 | 3 | 3 |
| 60 | 3 | 3 |
| 61 | 3 | 3 |
| 62 | 3 | 3 |
| 63 | 3 | 3 |
| 64 | 3 | 3 |
| 65 | 3 | 3 |
| 66 | 3 | 3 |
| 67 | 3 | 3 |
| 68 | 3 | 3 |
| 69 | 3 | 3 |
| 70 | 3 | 3 |
| 71 | 3 | 3 |
| 72 | 3 | 3 |
| 73 | 3 | 3 |
| 74 | 3 | 3 |
| 75 | 3 | 3 |
| 76 | 3 | 3 |
| 77 | 3 | 3 |
| 78 | 3 | 3 |
| 79 | 3 | 3 |
| 80 | 3 | 3 |
| 81 | 3 | 3 |
| 82 | 3 | 3 |
| 83 | 3 | 3 |
| 84 | 3 | 3 |
| 85 | 3 | 3 |
| 86 | 3 | 3 |
| 87 | 3 | 3 |
| 88 | 3 | 3 |
| 89 | 3 | 3 |
| 90 | 3 | 3 |
| 91 | 3 | 3 |
| 92 | 3 | 3 |
| 93 | 3 | 3 |

TABLE 29

[Example 4]
(4) PVA resin KM-118
B: Water/methanol = 4/6

| No. | 10 parts | 30 parts |
|-----|----------|----------|
| 1 | 3 | 3 |
| 2 | 3 | 3 |
| 3 | 3 | 3 |
| 4 | 3 | 3 |
| 5 | 3 | 3 |
| 6 | 3 | 3 |
| 7 | 3 | 3 |
| 8 | 3 | 3 |
| 9 | 3 | 3 |
| 10 | 3 | 3 |
| 11 | 3 | 3 |
| 12 | 3 | 3 |
| 13 | 3 | 3 |
| 14 | 3 | 3 |
| 15 | 3 | 3 |
| 16 | 3 | 3 |
| 17 | 3 | 3 |
| 18 | 3 | 3 |

TABLE 29-continued

[Example 4]
(4) PVA resin KM-118
B: Water/methanol = 4/6

| No. | 10 parts | 30 parts |
|---|---|---|
| 19 | 3 | 3 |
| 20 | 3 | 3 |
| 21 | 3 | 3 |
| 22 | 3 | 3 |
| 23 | 3 | 3 |
| 24 | 3 | 3 |
| 25 | 3 | 3 |
| 26 | 3 | 3 |
| 27 | 3 | 3 |
| 28 | 3 | 3 |
| 29 | 3 | 3 |
| 30 | 3 | 3 |
| 31 | 3 | 3 |
| 32 | 3 | 3 |
| 33 | 3 | 3 |
| 34 | 3 | 3 |
| 35 | 3 | 3 |
| 36 | 3 | 3 |
| 37 | 3 | 3 |
| 38 | 3 | 3 |
| 39 | 3 | 3 |
| 40 | 3 | 3 |
| 41 | 3 | 3 |
| 42 | 3 | 3 |
| 43 | 3 | 3 |
| 44 | 3 | 3 |
| 45 | 3 | 3 |
| 46 | 3 | 3 |
| 47 | 3 | 3 |
| 48 | 3 | 3 |
| 49 | 3 | 3 |
| 50 | 3 | 3 |
| 51 | 3 | 3 |
| 52 | 3 | 3 |
| 53 | 3 | 3 |
| 54 | 3 | 3 |
| 55 | 3 | 3 |
| 56 | 3 | 3 |
| 57 | 3 | 3 |
| 58 | 3 | 3 |
| 59 | 3 | 3 |
| 60 | 3 | 3 |
| 61 | 3 | 3 |
| 62 | 3 | 3 |
| 63 | 3 | 3 |
| 64 | 3 | 3 |
| 65 | 3 | 3 |
| 66 | 3 | 3 |
| 67 | 3 | 3 |
| 68 | 3 | 3 |
| 69 | 3 | 3 |
| 70 | 3 | 3 |
| 71 | 3 | 3 |
| 72 | 3 | 3 |
| 73 | 3 | 3 |
| 74 | 3 | 3 |
| 75 | 3 | 3 |
| 76 | 3 | 3 |
| 77 | 3 | 3 |
| 78 | 3 | 3 |
| 79 | 3 | 3 |
| 80 | 3 | 3 |
| 81 | 3 | 3 |
| 82 | 3 | 3 |
| 83 | 3 | 3 |
| 84 | 3 | 3 |
| 85 | 3 | 3 |
| 86 | 3 | 3 |
| 87 | 3 | 3 |
| 88 | 3 | 3 |
| 89 | 3 | 3 |
| 90 | 3 | 3 |
| 91 | 3 | 3 |
| 92 | 3 | 3 |
| 93 | 3 | 3 |

TABLE 30

[Example 4]
(4) PVA resin KM-118
C: Ethyl acetate

| No. | 10 parts | 30 parts |
|---|---|---|
| 1 | 3 | 3 |
| 2 | 3 | 3 |
| 3 | 3 | 3 |
| 4 | 3 | 3 |
| 5 | 3 | 3 |
| 6 | 3 | 3 |
| 7 | 3 | 3 |
| 8 | 3 | 3 |
| 9 | 3 | 3 |
| 10 | 3 | 3 |
| 11 | 3 | 3 |
| 12 | 3 | 3 |
| 13 | 3 | 3 |
| 14 | 3 | 3 |
| 15 | 3 | 3 |
| 16 | 3 | 3 |
| 17 | 3 | 3 |
| 18 | 3 | 3 |
| 19 | 3 | 3 |
| 20 | 3 | 3 |
| 21 | 3 | 3 |
| 22 | 3 | 3 |
| 23 | 3 | 3 |
| 24 | 3 | 3 |
| 25 | 3 | 3 |
| 26 | 3 | 3 |
| 27 | 3 | 3 |
| 28 | 3 | 3 |
| 29 | 3 | 3 |
| 30 | 3 | 3 |
| 31 | 3 | 3 |
| 32 | 3 | 3 |
| 33 | 3 | 3 |
| 34 | 3 | 3 |
| 35 | 3 | 3 |
| 36 | 3 | 3 |
| 37 | 3 | 3 |
| 38 | 3 | 3 |
| 39 | 3 | 3 |
| 40 | 3 | 3 |
| 41 | 3 | 3 |
| 42 | 3 | 3 |
| 43 | 3 | 3 |
| 44 | 3 | 3 |
| 45 | 3 | 3 |
| 46 | 3 | 3 |
| 47 | 3 | 3 |
| 48 | 3 | 3 |
| 49 | 3 | 3 |
| 50 | 3 | 3 |
| 51 | 3 | 3 |
| 52 | 3 | 3 |
| 53 | 3 | 3 |
| 54 | 3 | 3 |
| 55 | 3 | 3 |
| 56 | 3 | 3 |
| 57 | 3 | 3 |
| 58 | 3 | 3 |
| 59 | 3 | 3 |

TABLE 30-continued

[Example 4]
(4) PVA resin KM-118
C: Ethyl acetate

| No. | 10 parts | 30 parts |
|---|---|---|
| 60 | 3 | 3 |
| 61 | 3 | 3 |
| 62 | 3 | 3 |
| 63 | 3 | 3 |
| 64 | 3 | 3 |
| 65 | 3 | 3 |
| 66 | 3 | 3 |
| 67 | 3 | 3 |
| 68 | 3 | 3 |
| 69 | 3 | 3 |
| 70 | 3 | 3 |
| 71 | 3 | 3 |
| 72 | 3 | 3 |
| 73 | 3 | 3 |
| 74 | 3 | 3 |
| 75 | 3 | 3 |
| 76 | 3 | 3 |
| 77 | 3 | 3 |
| 78 | 3 | 3 |
| 79 | 3 | 3 |
| 80 | 3 | 3 |
| 81 | 3 | 3 |
| 82 | 3 | 3 |
| 83 | 3 | 3 |
| 84 | 3 | 3 |
| 85 | 3 | 3 |
| 86 | 3 | 3 |
| 87 | 3 | 3 |
| 88 | 3 | 3 |
| 89 | 3 | 3 |
| 90 | 3 | 3 |
| 91 | 3 | 3 |
| 92 | 3 | 3 |
| 93 | 3 | 3 |

TABLE 31

[Example 5]
(5) PVA resin C-506
A: 0.28% aqueous ammonia

| No. | 10 parts | 30 parts |
|---|---|---|
| 1 | 3 | 3 |
| 2 | 3 | 3 |
| 3 | 3 | 3 |
| 4 | 3 | 3 |
| 5 | 3 | 3 |
| 6 | 3 | 3 |
| 7 | 3 | 3 |
| 8 | 3 | 3 |
| 9 | 3 | 3 |
| 10 | 3 | 3 |
| 11 | 3 | 3 |
| 12 | 3 | 3 |
| 13 | 3 | 3 |
| 14 | 3 | 3 |
| 15 | 3 | 3 |
| 16 | 3 | 3 |
| 17 | 3 | 3 |
| 18 | 3 | 3 |
| 19 | 3 | 3 |
| 20 | 3 | 3 |
| 21 | 3 | 3 |
| 22 | 3 | 3 |
| 23 | 3 | 3 |
| 24 | 3 | 3 |
| 25 | 3 | 3 |
| 26 | 3 | 3 |
| 27 | 3 | 3 |
| 28 | 3 | 3 |
| 29 | 3 | 3 |
| 30 | 3 | 3 |
| 31 | 3 | 3 |
| 32 | 3 | 3 |
| 33 | 3 | 3 |
| 34 | 3 | 3 |
| 35 | 3 | 3 |
| 36 | 3 | 3 |
| 37 | 3 | 3 |
| 38 | 3 | 3 |
| 39 | 3 | 3 |
| 40 | 3 | 3 |
| 41 | 3 | 3 |
| 42 | 3 | 3 |
| 43 | 3 | 3 |
| 44 | 3 | 3 |
| 45 | 3 | 3 |
| 46 | 3 | 3 |
| 47 | 3 | 3 |
| 48 | 3 | 3 |
| 49 | 3 | 3 |
| 50 | 3 | 3 |
| 51 | 3 | 3 |
| 52 | 3 | 3 |
| 53 | 3 | 3 |
| 54 | 3 | 3 |
| 55 | 3 | 3 |
| 56 | 3 | 3 |
| 57 | 3 | 3 |
| 58 | 3 | 3 |
| 59 | 3 | 3 |
| 60 | 3 | 3 |
| 61 | 3 | 3 |
| 62 | 3 | 3 |
| 63 | 3 | 3 |
| 64 | 3 | 3 |
| 65 | 3 | 3 |
| 66 | 3 | 3 |
| 67 | 3 | 3 |
| 68 | 3 | 3 |
| 69 | 3 | 3 |
| 70 | 3 | 3 |
| 71 | 3 | 3 |
| 72 | 3 | 3 |
| 73 | 3 | 3 |
| 74 | 3 | 3 |
| 75 | 3 | 3 |
| 76 | 3 | 3 |
| 77 | 3 | 3 |
| 78 | 3 | 3 |
| 79 | 3 | 3 |
| 80 | 3 | 3 |
| 81 | 3 | 3 |
| 82 | 3 | 3 |
| 83 | 3 | 3 |
| 84 | 3 | 3 |
| 85 | 3 | 3 |
| 86 | 3 | 3 |
| 87 | 3 | 3 |
| 88 | 3 | 3 |
| 89 | 3 | 3 |
| 90 | 3 | 3 |
| 91 | 3 | 3 |
| 92 | 3 | 3 |
| 93 | 3 | 3 |

TABLE 32

[Example 5]
(5) PVA resin C-506
B: Water/methanol = 4/6

| No. | 10 parts | 30 parts |
|---|---|---|
| 1 | 3 | 3 |
| 2 | 3 | 3 |
| 3 | 3 | 3 |
| 4 | 3 | 3 |
| 5 | 3 | 3 |
| 6 | 3 | 3 |
| 7 | 3 | 3 |
| 8 | 3 | 3 |
| 9 | 3 | 3 |
| 10 | 3 | 3 |
| 11 | 3 | 3 |
| 12 | 3 | 3 |
| 13 | 3 | 3 |
| 14 | 3 | 3 |
| 15 | 3 | 3 |
| 16 | 3 | 3 |
| 17 | 3 | 3 |
| 18 | 3 | 3 |
| 19 | 3 | 3 |
| 20 | 3 | 3 |
| 21 | 3 | 3 |
| 22 | 3 | 3 |
| 23 | 3 | 3 |
| 24 | 3 | 3 |
| 25 | 3 | 3 |
| 26 | 3 | 3 |
| 27 | 3 | 3 |
| 28 | 3 | 3 |
| 29 | 3 | 3 |
| 30 | 3 | 3 |
| 31 | 3 | 3 |
| 32 | 3 | 3 |
| 33 | 3 | 3 |
| 34 | 3 | 3 |
| 35 | 3 | 3 |
| 36 | 3 | 3 |
| 37 | 3 | 3 |
| 38 | 3 | 3 |
| 39 | 3 | 3 |
| 40 | 3 | 3 |
| 41 | 3 | 3 |
| 42 | 3 | 3 |
| 43 | 3 | 3 |
| 44 | 3 | 3 |
| 45 | 3 | 3 |
| 46 | 3 | 3 |
| 47 | 3 | 3 |
| 48 | 3 | 3 |
| 49 | 3 | 3 |
| 50 | 3 | 3 |
| 51 | 3 | 3 |
| 52 | 3 | 3 |
| 53 | 3 | 3 |
| 54 | 3 | 3 |
| 55 | 3 | 3 |
| 56 | 3 | 3 |
| 57 | 3 | 3 |
| 58 | 3 | 3 |
| 59 | 3 | 3 |
| 60 | 3 | 3 |
| 61 | 3 | 3 |
| 62 | 3 | 3 |
| 63 | 3 | 3 |
| 64 | 3 | 3 |
| 65 | 3 | 3 |
| 66 | 3 | 3 |
| 67 | 3 | 3 |
| 68 | 3 | 3 |
| 69 | 3 | 3 |
| 70 | 3 | 3 |
| 71 | 3 | 3 |
| 72 | 3 | 3 |
| 73 | 3 | 3 |
| 74 | 3 | 3 |
| 75 | 3 | 3 |
| 76 | 3 | 3 |
| 77 | 3 | 3 |
| 78 | 3 | 3 |
| 79 | 3 | 3 |
| 80 | 3 | 3 |
| 81 | 3 | 3 |
| 82 | 3 | 3 |
| 83 | 3 | 3 |
| 84 | 3 | 3 |
| 85 | 3 | 3 |
| 86 | 3 | 3 |
| 87 | 3 | 3 |
| 88 | 3 | 3 |
| 89 | 3 | 3 |
| 90 | 3 | 3 |
| 91 | 3 | 3 |
| 92 | 3 | 3 |
| 93 | 3 | 3 |

TABLE 33

Example 5
(5) PVA resin C-506
C: Ethyl acetate

| No. | 10 parts | 30 parts | No. | 10 parts | 30 parts | No. | 10 parts | 30 parts | No. | 10 parts | 30 parts |
|---|---|---|---|---|---|---|---|---|---|---|---|
| 1 | 3 | 3 | 26 | 3 | 3 | 51 | 3 | 3 | 76 | 3 | 3 |
| 2 | 3 | 3 | 27 | 3 | 3 | 52 | 3 | 3 | 77 | 3 | 3 |
| 3 | 3 | 3 | 28 | 3 | 3 | 53 | 3 | 3 | 78 | 3 | 3 |
| 4 | 3 | 3 | 29 | 3 | 3 | 54 | 3 | 3 | 79 | 3 | 3 |
| 5 | 3 | 3 | 30 | 3 | 3 | 55 | 3 | 3 | 80 | 3 | 3 |
| 6 | 3 | 3 | 31 | 3 | 3 | 56 | 3 | 3 | 81 | 3 | 3 |
| 7 | 3 | 3 | 32 | 3 | 3 | 57 | 3 | 3 | 82 | 3 | 3 |
| 8 | 3 | 3 | 33 | 3 | 3 | 58 | 3 | 3 | 83 | 3 | 3 |
| 9 | 3 | 3 | 34 | 3 | 3 | 59 | 3 | 3 | 84 | 3 | 3 |
| 10 | 3 | 3 | 35 | 3 | 3 | 60 | 3 | 3 | 85 | 3 | 3 |
| 11 | 3 | 3 | 36 | 3 | 3 | 61 | 3 | 3 | 86 | 3 | 3 |

TABLE 33-continued

Example 5
(5) PVA resin C-506
C: Ethyl acetate

| No. | 10 parts | 30 parts | No. | 10 parts | 30 parts | No. | 10 parts | 30 parts | No. | 10 parts | 30 parts |
|---|---|---|---|---|---|---|---|---|---|---|---|
| 12 | 3 | 3 | 37 | 3 | 3 | 62 | 3 | 3 | 87 | 3 | 3 |
| 13 | 3 | 3 | 38 | 3 | 3 | 63 | 3 | 3 | 88 | 3 | 3 |
| 14 | 3 | 3 | 39 | 3 | 3 | 64 | 3 | 3 | 89 | 3 | 3 |
| 15 | 3 | 3 | 40 | 3 | 3 | 65 | 3 | 3 | 90 | 3 | 3 |
| 16 | 3 | 3 | 41 | 3 | 3 | 66 | 3 | 3 | 91 | 3 | 3 |
| 17 | 3 | 3 | 42 | 3 | 3 | 67 | 3 | 3 | 92 | 3 | 3 |
| 18 | 3 | 3 | 43 | 3 | 3 | 68 | 3 | 3 | 93 | 3 | 3 |
| 19 | 3 | 3 | 44 | 3 | 3 | 69 | 3 | 3 | | | |
| 20 | 3 | 3 | 45 | 3 | 3 | 70 | 3 | 3 | | | |
| 21 | 3 | 3 | 46 | 3 | 3 | 71 | 3 | 3 | | | |
| 22 | 3 | 3 | 47 | 3 | 3 | 72 | 3 | 3 | | | |
| 23 | 3 | 3 | 48 | 3 | 3 | 73 | 3 | 3 | | | |
| 24 | 3 | 3 | 49 | 3 | 3 | 74 | 3 | 3 | | | |
| 25 | 3 | 3 | 50 | 3 | 3 | 75 | 3 | 3 | | | |

TABLE 34

| Comparative Example | A Aqueous Ammonia | B Water/Methanol | C Ethyl Acetate |
|---|---|---|---|
| 1 | 2 | 2 | 1 |
| 2 | 1 | 1 | 1 |
| 3 | 1 | 1 | 3 |
| 4 | 1 | 1 | 3 |
| 5 | 1 | 1 | 3 |

TABLE 35

| Comparative Example | A Aqueous Ammonia | | B Water/Methanol | | C Ethyl Acetate | |
|---|---|---|---|---|---|---|
| | 10 parts | 30 parts | 10 parts | 30 parts | 10 parts | 30 parts |
| 6 | 2 | 2 | 2 | 2 | 1 | 1 |
| 7 | 2 | 2 | 2 | 2 | 1 | 1 |
| 8 | 1 | 1 | 1 | 1 | 3 | 3 |
| 9 | 1 | 1 | 1 | 1 | 3 | 3 |
| 10 | 1 | 1 | 1 | 1 | 3 | 3 |

TABLE 36

[Example 6] PVA resin KL-318

| No. | 5 parts | 10 parts |
|---|---|---|
| 1 | ⊙ | ⊙ |
| 2 | ⊙ | ⊙ |
| 3 | ⊙ | ⊙ |
| 4 | ⊙ | ⊙ |
| 5 | ⊙ | ⊙ |
| 6 | ⊙ | ⊙ |
| 7 | ⊙ | ⊙ |
| 8 | ⊙ | ⊙ |
| 9 | ⊙ | ⊙ |
| 10 | ⊙ | ⊙ |
| 11 | ⊙ | ⊙ |
| 12 | ⊙ | ⊙ |
| 13 | ⊙ | ⊙ |
| 14 | ⊙ | ⊙ |
| 15 | ⊙ | ⊙ |
| 16 | ⊙ | ⊙ |
| 17 | ⊙ | ⊙ |
| 18 | ⊙ | ⊙ |
| 19 | ⊙ | ⊙ |
| 20 | ⊙ | ⊙ |
| 21 | ⊙ | ⊙ |
| 22 | ⊙ | ⊙ |
| 23 | ⊙ | ⊙ |
| 24 | ⊙ | ⊙ |
| 25 | ⊙ | ⊙ |
| 26 | ⊙ | ⊙ |
| 27 | ⊙ | ⊙ |
| 28 | ⊙ | ⊙ |
| 29 | ⊙ | ⊙ |
| 30 | ⊙ | ⊙ |
| 31 | ⊙ | ⊙ |
| 32 | ⊙ | ⊙ |
| 33 | ⊙ | ⊙ |
| 34 | ⊙ | ⊙ |
| 35 | ⊙ | ⊙ |
| 36 | ⊙ | ⊙ |
| 37 | ⊙ | ⊙ |
| 38 | ⊙ | ⊙ |
| 39 | ⊙ | ⊙ |
| 40 | ⊙ | ⊙ |
| 41 | ⊙ | ⊙ |
| 42 | ⊙ | ⊙ |
| 43 | ⊙ | ⊙ |
| 44 | ⊙ | ⊙ |
| 45 | ⊙ | ⊙ |
| 46 | ⊙ | ⊙ |
| 47 | ⊙ | ⊙ |
| 48 | ⊙ | ⊙ |
| 49 | ⊙ | ⊙ |
| 50 | ○ | ⊙ |
| 51 | ○ | ⊙ |
| 52 | ○ | ⊙ |
| 53 | ○ | ⊙ |
| 54 | ○ | ⊙ |
| 55 | ○ | ⊙ |
| 56 | ○ | ⊙ |
| 57 | ○ | ⊙ |
| 58 | ○ | ⊙ |

TABLE 36-continued

[Example 6] PVA resin KL-318

| No. | 5 parts | 10 parts |
|---|---|---|
| 59 | ○ | ⊚ |
| 60 | ○ | ⊚ |
| 61 | ○ | ⊚ |
| 62 | ○ | ⊚ |
| 63 | ○ | ⊚ |
| 64 | ○ | ⊚ |
| 65 | ○ | ⊚ |
| 66 | ○ | ⊚ |
| 67 | ○ | ⊚ |
| 68 | ○ | ⊚ |
| 69 | ○ | ⊚ |
| 70 | ○ | ⊚ |
| 71 | ○ | ⊚ |
| 72 | ○ | ⊚ |
| 73 | ○ | ⊚ |
| 74 | ○ | ⊚ |
| 75 | ○ | ⊚ |
| 76 | ○ | ○ |
| 77 | ○ | ○ |
| 78 | ○ | ○ |
| 79 | ○ | ○ |
| 80 | ○ | ○ |
| 81 | ○ | ○ |
| 82 | ○ | ⊚ |
| 83 | ○ | ⊚ |
| 84 | ○ | ⊚ |
| 85 | ○ | ⊚ |
| 86 | ○ | ⊚ |
| 87 | ○ | ⊚ |
| 88 | ○ | ⊚ |
| 89 | ○ | ⊚ |
| 90 | ○ | ⊚ |
| 91 | ○ | ⊚ |
| 92 | ○ | ⊚ |
| 93 | ○ | ⊚ |

TABLE 37

[Example 7] PVA resin KM-118

| No. | 5 parts | 10 parts |
|---|---|---|
| 1 | ⊚ | ⊚ |
| 2 | ⊚ | ⊚ |
| 3 | ⊚ | ⊚ |
| 4 | ⊚ | ⊚ |
| 5 | ⊚ | ⊚ |
| 6 | ⊚ | ⊚ |
| 7 | ⊚ | ⊚ |
| 8 | ⊚ | ⊚ |
| 9 | ⊚ | ⊚ |
| 10 | ⊚ | ⊚ |
| 11 | ⊚ | ⊚ |
| 12 | ⊚ | ⊚ |
| 13 | ⊚ | ⊚ |
| 14 | ⊚ | ⊚ |
| 15 | ⊚ | ⊚ |
| 16 | ⊚ | ⊚ |
| 17 | ⊚ | ⊚ |
| 18 | ⊚ | ⊚ |
| 19 | ⊚ | ⊚ |
| 20 | ⊚ | ⊚ |
| 21 | ⊚ | ⊚ |
| 22 | ⊚ | ⊚ |
| 23 | ⊚ | ⊚ |
| 24 | ⊚ | ⊚ |
| 25 | ⊚ | ⊚ |
| 26 | ⊚ | ⊚ |
| 27 | ⊚ | ⊚ |
| 28 | ⊚ | ⊚ |
| 29 | ⊚ | ⊚ |
| 30 | ⊚ | ⊚ |
| 31 | ⊚ | ⊚ |
| 32 | ⊚ | ⊚ |
| 33 | ⊚ | ⊚ |
| 34 | ⊚ | ⊚ |
| 35 | ⊚ | ⊚ |
| 36 | ⊚ | ⊚ |
| 37 | ⊚ | ⊚ |
| 38 | ⊚ | ⊚ |
| 39 | ⊚ | ⊚ |
| 40 | ⊚ | ⊚ |
| 41 | ⊚ | ⊚ |
| 42 | ⊚ | ⊚ |
| 43 | ⊚ | ⊚ |
| 44 | ⊚ | ⊚ |
| 45 | ⊚ | ⊚ |
| 46 | ⊚ | ⊚ |
| 47 | ⊚ | ⊚ |
| 48 | ⊚ | ⊚ |
| 49 | ⊚ | ⊚ |
| 50 | ○ | ⊚ |
| 51 | ○ | ⊚ |
| 52 | ○ | ⊚ |
| 53 | ○ | ⊚ |
| 54 | ○ | ⊚ |
| 55 | ○ | ⊚ |
| 56 | ○ | ⊚ |
| 57 | ○ | ⊚ |
| 58 | ○ | ⊚ |
| 59 | ○ | ⊚ |
| 60 | ○ | ⊚ |
| 61 | ○ | ⊚ |
| 62 | ○ | ⊚ |
| 63 | ○ | ⊚ |
| 64 | ○ | ⊚ |
| 65 | ○ | ⊚ |
| 66 | ○ | ⊚ |
| 67 | ○ | ⊚ |
| 68 | ○ | ⊚ |
| 69 | ○ | ⊚ |
| 70 | ○ | ⊚ |
| 71 | ○ | ⊚ |
| 72 | ○ | ⊚ |
| 73 | ○ | ⊚ |
| 74 | ○ | ⊚ |
| 75 | ○ | ⊚ |
| 76 | ○ | ○ |
| 77 | ○ | ○ |
| 78 | ○ | ○ |
| 79 | ○ | ○ |
| 80 | ○ | ○ |
| 81 | ○ | ○ |
| 82 | ○ | ⊚ |
| 83 | ○ | ⊚ |
| 84 | ○ | ⊚ |
| 85 | ○ | ⊚ |
| 86 | ○ | ⊚ |
| 87 | ○ | ⊚ |
| 88 | ○ | ⊚ |
| 89 | ○ | ⊚ |
| 90 | ○ | ⊚ |
| 91 | ○ | ⊚ |
| 92 | ○ | ⊚ |
| 93 | ○ | ⊚ |

TABLE 38

[Example 8] PVA resin C-506

| No. | 5 parts | 10 parts |
|---|---|---|
| 1 | ⊚ | ⊚ |
| 2 | ⊚ | ⊚ |

TABLE 38-continued

[Example 8] PVA resin C-506

| No. | 5 parts | 10 parts |
|---|---|---|
| 3 | ⊙ | ⊙ |
| 4 | ⊙ | ⊙ |
| 5 | ⊙ | ⊙ |
| 6 | ⊙ | ⊙ |
| 7 | ⊙ | ⊙ |
| 8 | ⊙ | ⊙ |
| 9 | ⊙ | ⊙ |
| 10 | ⊙ | ⊙ |
| 11 | ⊙ | ⊙ |
| 12 | ⊙ | ⊙ |
| 13 | ⊙ | ⊙ |
| 14 | ⊙ | ⊙ |
| 15 | ⊙ | ⊙ |
| 16 | ⊙ | ⊙ |
| 17 | ⊙ | ⊙ |
| 18 | ⊙ | ⊙ |
| 19 | ⊙ | ⊙ |
| 20 | ⊙ | ⊙ |
| 21 | ⊙ | ⊙ |
| 22 | ⊙ | ⊙ |
| 23 | ⊙ | ⊙ |
| 24 | ⊙ | ⊙ |
| 25 | ⊙ | ⊙ |
| 26 | ⊙ | ⊙ |
| 27 | ⊙ | ⊙ |
| 28 | ⊙ | ⊙ |
| 29 | ⊙ | ⊙ |
| 30 | ⊙ | ⊙ |
| 31 | ⊙ | ⊙ |
| 32 | ⊙ | ⊙ |
| 33 | ⊙ | ⊙ |
| 34 | ⊙ | ⊙ |
| 35 | ⊙ | ⊙ |
| 36 | ⊙ | ⊙ |
| 37 | ⊙ | ⊙ |
| 38 | ⊙ | ⊙ |
| 39 | ⊙ | ⊙ |
| 40 | ⊙ | ⊙ |
| 41 | ⊙ | ⊙ |
| 42 | ⊙ | ⊙ |
| 43 | ⊙ | ⊙ |
| 44 | ⊙ | ⊙ |
| 45 | ⊙ | ⊙ |
| 46 | ⊙ | ⊙ |
| 47 | ⊙ | ⊙ |
| 48 | ⊙ | ⊙ |
| 49 | ⊙ | ⊙ |
| 50 | ○ | ⊙ |
| 51 | ○ | ⊙ |
| 52 | ○ | ⊙ |
| 53 | ○ | ⊙ |
| 54 | ○ | ⊙ |
| 55 | ○ | ⊙ |
| 56 | ○ | ⊙ |
| 57 | ○ | ⊙ |
| 58 | ○ | ⊙ |
| 59 | ○ | ⊙ |
| 60 | ○ | ⊙ |
| 61 | ○ | ⊙ |
| 62 | ○ | ⊙ |
| 63 | ○ | ⊙ |
| 64 | ○ | ⊙ |
| 65 | ○ | ⊙ |
| 66 | ○ | ⊙ |
| 67 | ○ | ⊙ |
| 68 | ○ | ⊙ |
| 69 | ○ | ⊙ |
| 70 | ○ | ⊙ |
| 71 | ○ | ⊙ |
| 72 | ○ | ⊙ |
| 73 | ○ | ⊙ |
| 74 | ○ | ⊙ |
| 75 | ○ | ⊙ |
| 76 | ○ | ○ |
| 77 | ○ | ○ |
| 78 | ○ | ○ |
| 79 | ○ | ○ |
| 80 | ○ | ○ |
| 81 | ○ | ○ |
| 82 | ○ | ⊙ |
| 83 | ○ | ⊙ |
| 84 | ○ | ⊙ |
| 85 | ○ | ⊙ |
| 86 | ○ | ⊙ |
| 87 | ○ | ⊙ |
| 88 | ○ | ⊙ |
| 89 | ○ | ⊙ |
| 90 | ○ | ⊙ |
| 91 | ○ | ⊙ |
| 92 | ○ | ⊙ |
| 93 | ○ | ⊙ |

TABLE 39

| Comparative Example | |
|---|---|
| 11 | X |
| 12 | X |
| 13 | X |

TABLE 40

| | 5 parts by weight | 10 parts by weight |
|---|---|---|
| Comparative Example | | |
| 14 | X | X |
| 15 | X | X |
| 16 | X | X |

The results of Tables 19 to 40 reveal that the films obtained from the coating materials formulated with the carbodiimide crosslinking agents of the invention have good water and chemical resistances.

Thus, the crosslinking agent of the invention has good miscibility and reactivity with polymer resins to be crosslinked, and the resultant film has good resistances to water, chemicals and wear.

What is claimed is:

1. A carbodiimide crosslinking agent comprising a decarbonated condensate of one or more diisocyanates selected from the group consisting of hexamethylene diisocyanate (HDI), hydrogenated xylylene diisocyanate ($H_6$XDI), xylylene diisocyanate (XDI), 2,2,4-trimethyl-hexamethylene diisocyanate (TMHDI), 1,12-diisocyanato-dodecane (DDI), norbornane diisocyanat+e (NBDI) and 2,4-bis-(8-isocyanatooctyl)-1,3-dioctyl cyclobutane (OCDI).

2. A crosslinking agent for polyvinyl alcohol comprising a water-soluble or dispersible carbodiimide compound consisting essentially of a condensate obtained by decarbonation condensation of a diisocyanate or a mixture of a diisocyanate and a triisocyanate wherein said condensate is blocked at terminal isocyanate groups with a hydrophilic group.

3. A crosslinking agent for polyvinyl alcohol according to claim 2, wherein said diisocyanate and said triisocyanate are selected from the group consisting of 4,4'- dicyclohexylmethane diisocyanate (HMDI), ditetramethylxylylene diisocyanate (TMXDI), isophorone isocyanate (IPDI), 2,4,6-triisopropylphenyl diisocyanate (TIDI), 4,4'-diphenylmethane diisocyanate (MDI), tolylene diisocyanate (TDI), hydrogenated tolylene diisocyanate (HTDI) and isocyanates having at least two isocyanates bonded to the carbon of the methylene group in the molecule.

4. A coating material comprising a polyvinyl alcohol and a water-soluble or dispersible carbodiimide compound consisting essentially of a condensate obtained by decarbonation condensation of a diisocyanate or a mixture of a diisocyanate and a triisocyanate wherein said condensate is blocked at terminal isocyanate groups with a hydrophilic group.

5. The coating material of claim 4 wherein said diisocyanate and said triisocyanate are selected from the group consisting of 4,4'-dicyclohexylmethane diisocyanate (HMDI), tetramethylxylylene diisocyanate (TMXDI), isophorone diisocyanate (IPDI), 2,4,6-triisopropylphenyl diisocyanate (TIDI), 4,4'-diphenylmethane diisocyanate (MDI), tolylene diisocyanate (TDI), hydrogenated tolylene diisocyanate (HTDI) and isocyanates having at least two isocyanates bonded to the carbon of the methylene group in the molecule.

6. The crosslinking agent of claim 2 wherein the diisocyanate is one or more diisocyanates selected from the group consisting of hexamethylene diisocyanate (HDI), hydrogenated xylylene diisocyanate ($H_6XDI$), xylylene diisocyanate (XDI), 2,2,4-trimethylhexamethylene diisocyanate (TMHDI), 1,12-diisocyanatododecane (DDI), norbornane diisocyanate (NBDI) and 2,4-bis-(8-isocyanato-octyl)-1,3-dioctyl cyclobutane (OCDI).

7. A process for crosslinking polyvinyl alcohol comprising combining polyvinyl alcohol with a water-soluble or dispersible carbodiimide compound consisting essentially of a condensate obtained by decarbonation condensation of a diisocyanate or a mixture of a diisocyanate and a triisocyanate wherein said condensate is blocked at terminal isocyanate groups with a hydrophilic group.

8. The process according to claim 7, wherein said diisocyanate and said triisocyanate are selected from the group consisting of 4,4'-dicyclohexylmethane diisocyanate (HMDI), tetramethylxylylene diisocyanate (TMXDI), isophorone diisocyanate (IPDI), 2,4,6-triisopropylphenyl diisocyanate (TIDI), 4,4'-diphenylmethane diisocyanate (MDI), tolylene diisocyanate (TDI), hydrogenated tolylene diisocyanate (HTDI) and isocyanates having at least two isocyanates bonded to the carbon of the methylene group in the molecule.

9. The process according to claim 7, wherein the diisocyanate is one or more diisocyanates selected from the group consisting of hexamethylene diisocyanate (HDI), hydrogenated xylylene diisocyanate ($H_6XDI$), xylylene diisocyanate (XDI), 2,2,4-trimethylhexamethylene diisocyanate (TMHDI), 1,12-diisocyanatododecane (DDI), norbornane diisocyanate (NBDI) and 2,4-bis-(8-isocyanato-octyl)-1,3-dioctyl cyclobutane (OCDI).

* * * * *